United States Patent
Xie et al.

(10) Patent No.: US 11,311,600 B2
(45) Date of Patent: Apr. 26, 2022

(54) METHODS FOR TREATING OBESITY

(71) Applicant: Marshall University Research Corporation, Huntington, WV (US)

(72) Inventors: Zijian Xie, Huntington, WV (US); Joseph I. Shapiro, Huntington, WV (US); Nader G. Abraham, Huntington, WV (US); Komal Sodhi, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 0 days.

(21) Appl. No.: 15/545,085

(22) PCT Filed: Jan. 29, 2016

(86) PCT No.: PCT/US2016/015676
§ 371 (c)(1),
(2) Date: Jul. 20, 2017

(87) PCT Pub. No.: WO2016/123493
PCT Pub. Date: Aug. 4, 2016

(65) Prior Publication Data
US 2018/0353569 A1    Dec. 13, 2018

Related U.S. Application Data

(60) Provisional application No. 62/109,816, filed on Jan. 30, 2015.

(51) Int. Cl.
*A61K 38/16* (2006.01)
*A61P 3/04* (2006.01)
*A61K 38/46* (2006.01)
*A61K 38/00* (2006.01)
*A61P 3/06* (2006.01)

(52) U.S. Cl.
CPC ............ *A61K 38/16* (2013.01); *A61K 38/005* (2013.01); *A61K 38/46* (2013.01); *A61P 3/04* (2018.01); *A61P 3/06* (2018.01); *C12Y 306/03009* (2013.01)

(58) Field of Classification Search
None
See application file for complete search history.

(56) References Cited

U.S. PATENT DOCUMENTS

| 8,283,441 B2 | 10/2012 | Xie et al. | |
|---|---|---|---|
| 8,691,947 B2 | 4/2014 | Xie et al. | |
| 2006/0094682 A1* | 5/2006 | Westwick | C12Q 1/485 514/44 A |
| 2010/0048545 A1 | 2/2010 | Jette et al. | |
| 2012/0031732 A1 | 2/2012 | Harrington | |
| 2014/0031419 A1 | 1/2014 | Xie et al. | |
| 2014/0187484 A1* | 7/2014 | Xie | C07K 14/4703 514/7.5 |
| 2015/0233925 A1 | 8/2015 | Xie et al. | |

FOREIGN PATENT DOCUMENTS

| WO | 2008/054792 A2 | 5/2008 |
|---|---|---|
| WO | 2010/071767 A2 | 6/2010 |

OTHER PUBLICATIONS

Kennedy et al. CD36 and Na/K-ATPase-a1 Form a Proinflammatory Signaling Loop in Kidney. Hypertension. 2013, vol. 61(1), p. 216-24.*
Proto-oncogene tyrosine-protein kinase Src. Last edited on Dec. 7, 2019. https://en.wikipedia.org/wiki/Proto-oncogene_tyrosine-protein_kinase_Src.*
Sylow, et al. (The Cancer Drug Dasatinib Increases PGC-1alpha in Adipose Tissue but Has Adverse Effects on Glucose Tolerance in Obese Mice. Endocrinology. Nov. 2016;157(11):4184-4191.*
European Patent Office, Extended European Search Report issued in corresponding Application No. EP 16 74 4186, dated Sep. 19, 2018.
Li, et al. "NaKtide, a Na/K-ATPase-derived peptide Src inhibitor, antagonizes ouabain-activated signal transduction in cultured cells." The Journal of biological chemistry 284, 21066-21076 (2009); published online Epub Jul. 31 (10.1074/jbc.M109.013821).
United States Patent and Trademark Office, International Search Report and Written Opinion issued in corresponding Application No. PCT/US16/15676, dated May 27, 2016.
Kennedy, et al. "CD36 and Na/K-ATPase-a1 Form a Proinflammatory Signaling Loop in Kidney." Hypertension . 2013, vol. 61(1), p. 216-24.
Lessard, et al. "Low abdominal subcutaneous preadipocyte adipogenesis is associated with visceral obesity, visceral adipocyte hypertrophy, and a dysmetabolic state." Adipocyte. 2014, vol. 3(3), p. 197-205 Epub Jun. 3, 2014.
Bays, et al. "Obesity, adiposity, and dyslipidemia: a consensus statement from the National Lipid Association." J Clin Lipidol. 2013, vol. 7(4), p. 304-83.
Sodhi, et al. "pNaKtide inhibits Na/K-ATPase reactive oxygen species amplification and attenuates adipogenesis." Sci. Adv. 2015; 1:e1500781.
Cao, et al. "EET intervention on Wnt1, NOV, and HO-1 signaling prevents obesity-induced cardiomyopathy in obese mice." Am J Physiol Heart Circ Physiol. 2017; 313(2): H368-H380.
Sodhi, et al. "pNaKtide Attenuates Steatohepatitis and Atherosclerosis by Blocking Na/K-ATPase/ROS Amplification in C57Bl6 and ApoE Knockout Mice Fed a Western Diet." Scientific Reports 7: 193 [DOI: 10.1038/s41598-017-00306-5.

(Continued)

*Primary Examiner* — Maury A Audet
(74) *Attorney, Agent, or Firm* — Stites & Harbison, PLLC; Terry L. Wright

(57) ABSTRACT

Methods for treating obesity are provided and include administering a polypeptide antagonist of a Na/K ATPase/Src receptor complex to a subject in need thereof. Methods for reducing adiposity and adipogenesis are also provided and make use of a polypeptide antagonist of a Na/K ATPase/Src receptor complex to a subject.

15 Claims, 15 Drawing Sheets

Specification includes a Sequence Listing.

(56) References Cited

OTHER PUBLICATIONS

Srikanthan, et al. "The Role of Na/K-ATPase Signaling in Oxidative Stress Related to Obesity and Cardiovascular Disease." Molecules 2016, 21, 1172; doi:10.3390/molecules21091172.
Sharma, et al. "Investigating Molecular Connections of Non-alcoholic Fatty Liver Disease with Associated Pathological Conditions in West Virginia for Biomarker Analysis." J Clin Cell Immunol. 2017; 8(5): doi:10.4172/2155-9899.1000523.
Goguet -Rubio, et al. "Existence of a Strong Correlation of Biomarkers and miRNA in Females with Metabolic Syndrome and Obesity in a Population of West Virginia." Int. J. Med. Sci. 2017; 14(6): 543-553.
Srikanthan, et al. "Systematic Review of Metabolic Syndrome Biomarkers: A Panel for Eady Detection, Management, and Risk Stratification in the West Virginian Population." Int. J. Med. Sci. 2016; 13(1): 25-38.
Bartlett, et al. "The Role of Na/K-ATPase Signaling in Oxidative Stress Related to Aging: Implications in Obesity and Cardiovascular Disease." Int. J. Mol. Sci. 2018; 19(7): 2139.
Nawab, et al. "Spin Trapping: A Review for the Study of Obesity Related Oxidative Stress and Na+/K+-ATPase." J. Clin Cell Immunol. 2017; 8(3): doi:10.4172/2155-9899.1000505.
Peterson, et al. "Oxidized HDL is a potent inducer of adipogenesis and causes activation of the Ang-II and 20-HETE systems in human obese females." Prostaglandins and Other Lipid Mediators 123 (2016) 68-77.
Sodhi, et al. "Role of Serum Biomarkers in Early Detection of Non-Alcoholic Steatohepatitis and Fibrosis in West Virginian Children." J Clin Cell Immunol. 2016 7(1).
Lakhani, et al. "Phenotypic Alteration of Hepatocytes in Non-Alcoholic Fatty Liver Disease." Int. J. Med. Sci. 2018, 1591-1599.
Sodhi, et al. "Uric Acid-Induced Adipocyte Dysfunction Is Attenuated by HO-1 Upregulation: Potential Role of Antioxidant Therapy to Target Obesity." Stem Cells International 2016, 1-11.
Sodhi, et al. "Fructose Mediated Non-Alcoholic Fatty Liver Is Attenuated by HO-1-SIRT1 Module in Murine Hepatocytes and Mice Fed a High Fructose Diet." PLOS ONE. 2015. DOI:101371/journal.pone.0128648.
Khitan, et al. "HO-1 Upregulation Attenuates Adipocyte Dysfunction, Obesity, and Isoprostane Levels in Mice Fed High Fructose Diets." Journal of Nutrition and Metabolism. 2014. http://dx.doi.org/10.1155/2014/980547.
Ogu, et al. "Stroke volume and proteinuria in obesity-related glomerulopathy: potential role in pathogenesis and choice of anti-hypertensive regimen." The Journal of Clinical Hypertension. 2018.
Vanella, et al. "Increased heme-oxygenase 1 expression in mesenchymal stem cell-derived adipocytes decreases differentiation and lipid accumulation via upregulation of the canonical Wnt signaling cascade." Stem cell research & therapy 4, 28 (2013)10.1186/scrt176).
Bartlett, et al. "Uremic Toxins Activates Na/K-ATPase Oxidant Amplification Loop Causing Phenotypic Changes in Adipocytes in In Vitro Models." Int J. Mol. Sci. 2018, 19, 2685.
Petterson, et al. "Oxidized HDL, Adipokines, and Endothelial Dysfunction: A Potential Biomarker Profile for Cardiovascular Risk in Women with Obesity." 2019.
European Patent Office, Examination Report issued in corresponding Application No. EP 16 744 186.4, dated Jan. 22, 2020. The claims on file in the European application at the date of issuance are attached.
Li, Z., et al. "NaKtide, a Na/K-ATPase-derived Peptide Src Inhibitor, Antagonizes Ouabain-activated Signal Transduction in Cultured Cells," The Journal of Biological Chemistry, vol. 284, No. 31, Jul. 31, 2009.

* cited by examiner

METHODS FOR TREATING OBESITY

RELATED APPLICATIONS

This application claims priority from U.S. Provisional Application Ser. No. 62/109,816, filed Jan. 30, 2015, the entire disclosure of which is incorporated herein by this reference.

GOVERNMENT SUPPORT

This invention was made with government support under grant numbers HL109015, HL071556, HL105649, HL55601, and HL34300 awarded by the National Institutes of Health. The government has certain rights in the invention.

TECHNICAL FIELD

The present invention relates to methods for treating obesity. In particular, the present invention relates to methods for treating obesity that make use of a polypeptide that inhibits the receptor function of the Na/K-ATPase and Src complex.

BACKGROUND

The number of overweight individuals worldwide has grown markedly, leading to an increase in obesity-related health problems and associated morbidity and mortality. Oxidative stress in adipose tissue is an important pathogenic mechanism leading to maintenance of the obesity phenotype—associated metabolic syndrome. It has recently been observed that the development of obesity can be markedly affected by the manipulation of either the systemic redox state or the redox state of adipocytes alone. Specifically, manipulation of the redox state of adipocytes by the targeted transfection of anti-oxidant genes to adipocytes alters their phenotype as well as reduces total body fat stores and ameliorates metabolic abnormalities.

Dysfunctional adipogenesis is, in fact, one of the hallmarks of chronic obesity and is characterized by increased lipid accumulation and altered endocrine function of the adipose tissue. Peroxisome proliferator—activated receptor gamma (PPARγ) is a master regulator of adipogenesis and activates the expression of genes, such as fatty acid synthase (FAS), to trigger the synthesis of fatty acids and triglycerides. Mesoderm—specific transcript, (MEST), when upregulated, results in adipocyte enlargement during adipose tissue expansion, which is associated with increased release of inflammatory adipocytokines and enhanced insulin resistance. Adipose tissue regulates energy metabolism via secretion of soluble factors such as adiponectin and tumor necrosis factor α (TNFα). Dysregulated production of these adipocytokines participates in the pathogenesis of obesity-associated metabolic syndrome.

Accordingly, compositions and methods for treating obesity, including compositions and methods that treat the underlying causes of obesity, would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

The presently-disclosed subject matter includes methods for treating obesity. In particular, the presently-disclosed subject matter includes methods for treating obesity that make use of a polypeptide that inhibits the receptor function of the Na/K-ATPase and Src complex.

In some embodiments, a method for treating obesity is provided that includes administering a polypeptide antagonist of a Na/K ATPase/Src receptor complex to a subject in need thereof. In some embodiments, the polypeptide anatagonist comprises the sequence of SEQ ID NO: 1, or a fragment, and/or variant thereof. In some embodiments, the polypeptide anatagonist further includes a cell penetrating polypeptide encoded by an amino acid sequence selected from the group consisting of SEQ ID NOS: 2-3. In some embodiments, the administering step includes oral administration, transdermal administration, administration by inhalation, nasal administration, topical administration, intraaural administration, rectal administration, intravenous administration, intramuscular administration, subcutaneous administration, and/or intravitreous administration.

With further respect to the administration of the polypeptide antagonist, in some embodiments, administering the polypeptide antagonist (e.g., the polypeptide of SEQ ID NO: 1) reduces one or more symptoms and/or characteristics associated with obesity. For example, in some embodiments, administering the polypeptide antagonist decreases lipid accumulation in a cell of the subject. In some embodiments, administering the polypeptide antagonist decreases an amount of adipogenesis, decreases an amount of adipocyte differentiation, and/or increases an amount of small adipocytes. Further, in some embodiments, administering the polypeptide antagonist decreases an amount of inflammatory cytokines, such as tumor necrosis factor α (TNFα). In other embodiments, administering the polypeptide increases an amount of adiponectin and/or reduces an expression level of an adipogenic marker, such as FAS, MEST, and PPARγ.

Further provided, in some embodiments of the presently-disclosed subject matter, are methods for reducing an amount of adiposity in a subject that include the administration of a polypeptide antagonist of a Na/K ATPase/Src receptor complex (e.g., a polypeptide of SEQ ID NO: 1) to a subject in need thereof. In some of these additional embodiments, administering the polypeptide reduces an amount of visceral fat and/or an amount of subcutaneous fat in the subject.

Still further provided, in some embodiments of the presently-disclosed subject matter are methods for reducing adipogenesis. In some embodiments, a method for reducing adipogenesis is provided that comprises contacting a cell with a polypeptide antagonist of a Na/K ATPase/Src receptor complex (e.g., a polypeptide of SEQ ID NO: 1). In some embodiments, the cell is a pre-adipocyte.

Further features and advantages of the present invention will become evident to those of ordinary skill in the art after a study of the description, figures, and non-limiting examples in this document.

BRIEF DESCRIPTION OF THE DRAWINGS

FIG. 1A shows representative images of the mouse preadipocytes. FIG. 1B is a graph showing quantitative data from the oil red staining expressed as means±SE, n=7, *p<0.05 vs. control. FIGS. 1C-1D include graphs showing dose-dependent increases in small lipid droplets and dose-dependent decreases in large lipid droplets subsequent to pNaKtide administration. FIG. 1E is a graph showing superoxide levels, a marker for oxidative stress, were reduced significantly by pNaKtide in 3T3L1 cells.

(FIG. 2A) an image and graph showing adiponectin levels determined in conditioned media obtained from 3T3L1 cells after treating with pNaKtide for 7 days, where cells were treated with varying concentrations of pNaKtide and 0.7 µM of pNaKtide was determined to be the optimal concentration for increasing adiponectin levels (results are means±SE, n=4, *p<0.05 vs. control); and graphs showing the expression of (FIG. 2B) FAS, (FIG. 2C) MEST, and (FIG. 2D) PPARγ as determined by Western blot analysis in 3T3L1 cells after treating with pNaKtide (0.7 µM) for 7 days, where quantitative densitometry evaluation of the proteins ratio was determined (data are expressed as means±SE, n=6, *p<0.05 vs. control).

(FIG. 5C) western blot and densitometry analysis of adiponectin expression (results are means±SE, n=7/group, *p<0.05 vs. control, # vs. HF; data are shown as mean band density normalized to β-actin).

(FIG. 6A) HOMA-IR; (FIG. 6B) Glucose Tolerance Test; (FIG. 6C) Thiobarbituric acid reactive substance (TBARS), a marker of oxidative injury that was measured in visceral adipose tissue; and (FIG. 6D) Plasma adiponectin levels, where results are means±SE, n=7-14/group, *p<0.05 vs. control, # vs. HF. Further included are graphs showing the effect of pNaKtide in fat tissue in mice fed a high-fat diet, including graphs showing: (FIG. 6E) protein carbonylation, (FIG. 6F) phosphorylation of c-Src; and (FIG. 6G) phosphorylation of ERK1/2, where results are Means±SE, n=4-7/group, **p<0.01 vs. control (CTR), # p<0.01 vs. high-fat diet (HF).

BRIEF DESCRIPTION OF THE SEQUENCE LISTING

Figure 1A:
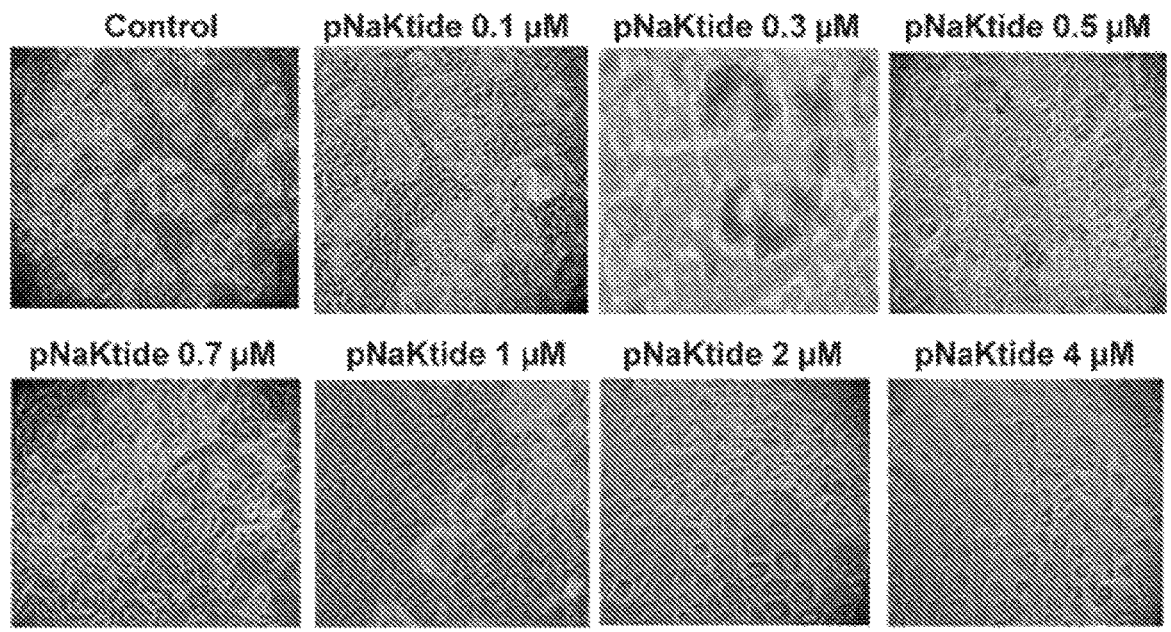
FIGS. 1A-1E include images and graphs showing the effect of increasing pNaKtide concentrations on adipogenesis in mouse preadipocytes. Adipogenesis was measured as the relative absorbance of Oil Red O at day 7 after inducing adipogenesis.

SEQ ID NO: 1 is an amino acid sequence of an embodiment of a polypeptide in accordance with the presently-disclosed subject matter (NaKtide);

SEQ ID NO: 2 is an amino acid sequence of a TAT cell penetrating peptide;

SEQ ID NO: 3 is an amino acid sequence of a penetratin (AP) cell penetrating peptide; and SEQ ID NO: 4 is an amino acid sequence of the N-terminal poly-lysine domain of the a1 subunit of Na/K-ATPase (AlN); and SEQ ID NO: 5 is another amino acid sequence of an embodiment of a polypeptide in accordance with the presently-disclosed subject matter (pNaKtide).

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

It will be understood that various details of the presently disclosed subject matter can be changed without departing from the scope of the subject matter disclosed herein. Furthermore, the description provided herein is for the purpose of illustration only, and not for the purpose of limitation.

Additionally, while the terms used herein are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although many methods, devices, and materials similar or equivalent to those described herein can be used in the practice or testing of the presently-disclosed subject matter, representative methods, devices, and materials are now described.

Furthermore, following long-standing patent law convention, the terms "a", "an", and "the" refer to "one or more" when used in this application, including the claims. Thus, for example, reference to "a polypeptide" includes a plurality of such polypeptides, and so forth. Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes methods for treating obesity. In particular, the presently-disclosed subject matter includes methods for treating obesity that make use of a polypeptide that inhibits the receptor function of the Na/K-ATPase and Src complex.

The Na/K-ATPase is a member of P-type ATPase. It resides in the plasma membrane and transports Na+ and K+ ions across cell membrane by hydrolyzing ATP. The functional Na/K-ATPase consists of α and β subunits, and several isoforms have been identified for each subunit. It has been observed that in addition to the ion pumping function, the α1 subunit also serves a scaffolding function with sarcoma—related kinase (Src), allowing conformational changes in the Na/K-ATPase to affect a signaling cascade. An antagonistic polypeptide sequence from the nucleotide-binding (N) domain of that a subunit has been identified, which binds the kinase domain of Src, tonically inhibiting its function. However, when the conformation of the al subunit is changed by the binding of cardiotonic steroids, this inhibition may be released, resulting in the activation of Src. The Na/K-ATPase therefore controls signaling through regulating Src with downstream modulation of the epithelial growth factor receptor (EGFR) and ultimately reactive oxygen species (ROS). Moreover, it has further been observed that the α1 subunit of the Na/K-ATPase can also act as a receptor for some ROS and potentially serve as a feed-forward amplifier. In this regard, a cell permeant NaKtide (pNaKtide) has been previously designed and was found to specifically inhibit cardiotonic steroid-induced Src activation. It has now been surprisingly discovered, however, that that pNaKtide can significantly attenuate Na/K-ATPase-modulated ROS amplification within the adipocyte and attenuate the development of adiposity and an obesity phenotype. More particularly, it has been observed that that the pNaKtide attenuates oxidant stress and lipid accumulation in a dose-dependent manner, reduces body weight gain, and improves insulin sensitivity.

The term "obesity," as used herein, refers to conditions in which excess body fat has accumulated to the extent that it may have a negative effect on health, which can, in turn, lead to reduced life expectancy and/or increased health problems. In certain instances, a subject can be considered obese when their body mass index (BMI), a measurement obtained by dividing a subject's weight by the square of the person's height, is greater than 20 kg/m$^2$, 21 kg/m$^2$, 22 kg/m$^2$, 23 kg/m$^2$, 24 kg/m$^2$, 25 kg/m$^2$, 26 kg/m$^2$, 27 kg/m$^2$, 28 kg/m$^2$, 29 kg/m$^2$, or 30 kg/m$^2$. Obesity can also coincide with conditions such as, but not limited to, hyperinsulinemia, insulin resistance, diabetes, hypertension, and dyslipidemia. Obesity can further be a risk factor for cardiovascular disease. In some instances, obesity can also be characterized by one or more of fasting glucose levels of at least 100 mg/dl, plasma triglyceride levels of at least 150 mg/dl, HDL cholesterol below 40 mg/dl in men and below 50 mg/dl in women, blood pressure of at least 130/85 mm Hg, and abdominal waist circumference of greater than 40 inches for men and greater than 35 inches for women.

As noted, embodiments of the presently-disclosed subject matter make use of a polypeptide to treat obesity. In some embodiments, the polypeptide can include a polypeptide that inhibits the receptor function of the Na/K-ATPase and Src complex. In some embodiments, the polypeptide is an antagonist for the receptor function of the Na/K-ATPase and Src complex.

The terms "polypeptide," "protein," and "peptide" are used interchangeably herein to refer to a polymer of amino acids regardless of its size or function. The terms "protein," "polypeptide," and "peptide" are used interchangeably herein to also refer to a gene product, homologs, orthologs, paralogs, fragments, any protease derived peptide (fragment), and other equivalents, variants, and analogs of a polymer of amino acids.

In some embodiments, the polypeptides are comprised of the sequence of SEQ ID NO: 1 (SATWLALSRIAGLCN-RAVFQ; NaKtide), or fragments, and/or variants thereof. The terms "polypeptide fragment" or "fragment" when used in reference to such a polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus of the reference polypeptide, the carboxy-terminus of the reference polypeptide, or both. Polypeptide fragments can also be inclusive of "functional fragments," in which case the fragment retains some or all of the activity of the reference polypeptide.

The term "variant," as used herein, refers to an amino acid sequence that is different from the reference polypeptide by one or more amino acids. In some embodiments, a variant polypeptide may differ from a reference polypeptide by one or more amino acid substitutions. For example, a NaKtide polypeptide variant can differ from the NaKtide polypeptide of SEQ ID NO: 1 by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide.

In some embodiments, the present polypeptides include polypeptides that share at least 75% homology with the NaKtide polypeptide of SEQ ID NO: 1. In some embodiments, the polypeptides share at least 85% homology with the NaKtide polypeptide of SEQ ID NO: 1. In some embodiments, the polypeptides share at least 90% homology with the NaKtide polypeptide of SEQ ID NO: 1. In some embodiments, the polypeptides share at least 95% homology with the NaKtide polypeptide of SEQ ID NO: 1.

"Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). [BLAST nucleotide searches are performed with the NBLAST program, score+ 100, wordlength=12, to obtain nucleotide sequences homologous to a nucleic acid molecule of the invention. BLAST protein searches are performed with the)(BLAST program, score=50, word length=3, to obtain amino acid sequences homologous to a reference polypeptide (e.g., SEQ ID NO: X). To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g.,)(BLAST and NBLAST) are used. In this regard, reference is made to the most recent version of the programs that are available as of Jul. 19, 2012.

Embodiments of the present polypeptides can further comprise one or more leader sequences, and, in some embodiments the leader sequences include, but are not limited to, cell penetrating peptides (CPPs). The term "cell penetrating peptide" (CPP) is used herein to generally refer to short peptides that can or that assist in facilitating the transport of molecular cargo across plasma membranes found in a cell. In some instances, the molecular cargo includes another polypeptide, such as the polypeptides described herein. Of course, the cell penetrating peptides can be conjugated to the molecular cargo (e.g., polypeptide) via any number of means, including covalent bonds and/or non-covalent bonds. In a number of instances, however, such cell penetrating peptides will often include a relatively high concentration of positively-charged amino acids, such as lysine and arginine, and will have a sequence that contains an alternating pattern of charged (polar) and non-charged amino acids.

In some embodiments of the presently-disclosed subject matter, an exemplary leader sequence or cell-penetrating peptide can include the trans-activating transcriptional activator (TAT) cell penetrating peptide, which is represented by the sequence of SEQ ID NO: 2 (GRKKRRQRRRPPQ). Another exemplary leader sequence includes penetratin (AP), which is represented by the sequence of SEQ ID NO: 3 (RQIKIWFQNRRMKWKK). Yet another exemplary leader sequence includes an amino acid sequence encoding the N-terminal poly-lysine domain of the α1 subunit of Na/K-ATPase (AlN), which is represented by the sequence of SEQ ID NO: 4 (KKGKKGKK). Those of ordinary skill will appreciate though that other leader sequences, including other cell penetrating peptides, can also be used in conjunction with the presently-disclosed polypeptides. In some embodiments, a polypeptide including a leader sequence, such as a cell penetrating peptide, attached to the NaKtide sequence of SEQ ID NO: 1 is referred to herein as a pNaKtide (e.g., SEQ ID NO: 5; GRKKRRQRRRPPQSATWLALSRIAGLCNRAVFQ, which includes the TAT cell penetrating peptide of SEQ ID NO: 2 fused to the NaKtide sequence of SEQ ID NO: 1).

The presently-disclosed subject matter further includes and makes use of pharmaceutical compositions comprising the polypeptides described herein as well as a pharmaceutically-acceptable carrier. Indeed, when referring to certain embodiments herein, the terms "polypeptide" and/or "composition" may or may not be used to refer to a pharmaceutical composition that includes the polypeptide.

The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly (orthoesters) and poly (anhydrides). Depending upon the ratio of polypeptide to biodegradable polymer and the nature of the particular biodegradable polymer employed, the rate of polypeptide release can be controlled. Depot injectable formulations can also be prepared by entrapping the polypeptide in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the polypeptides can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose, or gelatin-free binding agents); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

As noted, the presently-disclosed subject matter includes methods for treating obesity with a polypeptide. Some embodiments of methods include administering one of the presently-disclosed polypeptides to a subject in need thereof. In some embodiments, the polypeptide can treat obesity by inhibiting the receptor function of the Na/K-ATPase and Src complex, and in some embodiments, the polypeptides inhibit the receptor function by acting as an antagonist of the Na/K-ATPase and Src complex.

The term "inhibiting" or "inhibition" does not necessarily refer to the ability to completely inactivate all target biological activity in all cases. Rather, the skilled artisan will understand that the term "inhibiting" as well as the term "reduction" refers to decreasing biological activity of a target, such as can occur when a ligand binds a site of the target, a protein in a biochemical pathway of the target is blocked or the expression of such a protein is reduced, a non-native complexes with a target, or the like. Such decreases in biological activity can be determined relative to a control, wherein the control can be representative of an environment in which a polypeptide of the presently-disclosed subject matter is not administered. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In this regard, the terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes: palliative treatment, or treatment designed for the relief of symptoms rather than the curing of the disease, pathological condition, or disorder; preventative treatment, or treatment directed to minimizing or partially or completely inhibiting the development of the associated disease, pathological condition, or disorder; and supportive treatment, or treatment employed to supplement another therapy directed toward the improvement of the associated disease, pathological condition, or disorder.

The treatment of obesity can be measured and quantified in several different ways and by taking into account several characteristics of obesity. In some embodiments, treatment of obesity can be measured and quantified by, among other things, decreased superoxide, lipogenesis, adipocyte differentiation, or a combination thereof. Alternatively or additionally, treatment of obesity can be characterized by an increase in small adipocytes. Treatment of obesity can also be characterized by a decrease in lipid accumulation, a decrease in inflammatory cytokine level, and/or an increase in adiponectin levels. Such measurements and quantifications can be performed by any number of methods known to those skilled in the art. In some embodiments, the increases and/or decreases described herein can be in reference to a control subject suffering from obesity and that has not been treated with one of the presently-disclosed polypeptides.

In some instances, treatment of obesity can include eliminating characteristic qualities of obesity. For example, in some embodiments, treatment of obesity can cause a subject to achieve one or more of fasting glucose levels below 100 mg/dl, plasma triglyceride levels below 150 mg/dl, HDL cholesterol above 40 mg/dl in men and above 50 mg/dl in women, blood pressure below 130/85 mm Hg, abdominal waist circumference lower than 40 inches for men and lower than 35 inches for women, and a Body Mass Index lower than 30 kg/m$^2$.

With further respect to the methods described herein, in some embodiments, the administering of a polypeptide antagonist in accordance with the presently-disclosed subject matter reduces an amount of an adipogenic marker in a subject or, in other words, a molecule, such as a polypeptide or mRNA, that is useful as an indicator of the differentiation of pre-adipocytes into adipocytes (i.e., adipogenesis). In some embodiments, such an adipogenic marker is selected from fatty acid synthase (FAS), mesoderm-specific transcript, (MEST), peroxisome proliferator-activated receptor gamma (PPARγ), and combinations thereof. In some embodiments of the presently-disclosed methods, adipogenesis is reduced by contacting a cell with a polypeptide antagonist of the presently-disclosed subject matter. In some embodiments, the cell is a pre-adipocyte.

In some embodiments of the methods described herein, administering the polypeptide reduces an amount of adiposity or, in other words, the accumulation of fat and lipids in the body of a subject. In some embodiments, the administration of the polypeptide reduces an amount of visceral fat and/or an amount of subcutaneous fat in a subject.

In this regard, the term "administering" is not particularly limited and refers to any method of providing a polypeptide and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The present methods can be performed on a wide variety of subjects. Indeed, the term "subject" as used herein is also not particularly limited. The term "subject" is inclusive of vertebrates, such as mammals, and the term "subject" can include human and veterinary subjects. Thus, the subject of the herein disclosed methods can be a human, non-human primate, horse, pig, rabbit, dog, sheep, goat, cow, cat, guinea pig, rodent, or the like. The term does not denote a particular age or sex. Thus, adult and newborn subjects, as well as fetuses, whether male or female, are intended to be covered.

The presently-disclosed subject matter is further illustrated by the following specific but non-limiting examples.

EXAMPLES

Materials and Methods for Examples 1-4
Experimental Design for In Vitro Experiment.

Frozen mouse pre-adipocytes (3T3L1) were resuspended in a α-minimal essential medium supplemented with 10% heat inactivated fetal bovine serum and 1% antibiotic/antimycotic solution. The cultures were maintained at 37° C. in a 5% $CO_2$ incubator and the medium was changed after 48 h and every 3~4 days thereafter. When the 3T3L1 cells were confluent, the cells were recovered by the addition of trypsin. 3T3L1 cells (Passage 2-3) were plated in 96 and 24 well plates at a density of 10,000 cells/cm$^2$ and cultured in α-MEM until 80% confluence was achieved. The medium was replaced with adipogenic medium, and the cells were cultured for an additional 7 days. Cells were treated every day with 0.1, 0.3, 0.5, 0.7, 1, 2 and 4 µM of pNaKtide respectively. After 7 days, cells were stained with Oil Red O solution to study adipogenesis as described previously.

Measurement of Lipid Droplet Size.

Cell size was measured using ImagePro Analyzer. The classification of the size of lipid droplets was based on size by area (pixels) as described previously.

Measurement of Superoxide Levels for In Vitro Experiment.

3T3L1 adipocytes were cultured on 96-well plates until they achieved approximately 70% confluence. After treatment with 0.1, 0.3, 0.5, 0.7, 1, 2 and 4 µM of pNaKtide for 72 hours, the cells were incubated with 10 µM dihydroethidium (DHE) for 30 min at 37° C. Fluorescence intensity was measured using a Perkin-Elmer Luminescence Spectrometer at excitation/emission filters of 530/620 nm.

Experimental Design for In Vivo Experiment.

All animal studies were approved by the Marshall University Animal Care and Use Committee in accordance with the National Institutes of Health Guidelines for Care and Use of Laboratory Animals. C57BL6 mice (6-8 weeks old, male) were purchased from Jackson Laboratory. Upon arrival to the Byrd Biotechnology Center, ARF, Animal Research Facility, mice were placed in cages and were fed normal chow diet and had access to water ad libitum. High fat (HF) diet was purchased commercially from Bio-SERV, Frenchtown, N.J. High fat diet contained 58% fat from lard, 25.6% carbohydrate, and 16.4% protein yielding 23.4 KJ/g. After 4 weeks of HF diet, the animals were divided into 4 groups and treatment was done for 8 weeks as follows: pNaKtide (dissolved in saline and injected I.P) at a dose of 0, 1, 5 and 25 mg/kg every 8 days. The body weight was measured every week. At the end of the 12-week period, mice were placed on an 8-hour fast, anesthetized with sodium pentobarbital (65 mg/kg, I.P.) and blood was obtained from the tail vein for measurement of glucose using a glucometer and measurement of insulin using ELISA assay kit (Abcam, Cambridge, Mass.). At the time of sacrifice the body weight, visceral, subcutaneous fat content and liver weight of all mice was measured. Blood samples were collected for adiponectin levels. Visceral adipose tissue was flash frozen in liquid nitrogen and maintained at −80° C. until assayed.

An additional group in which pNaKtide was administered at 25 mg/kg I.P. every 2 days (N=7) was also studied. These animals had less attenuation of weight gain than the 25 mg/kg I.P. every 8 days group, but at the time of sacrifice, it was clear that these animals had retained significant fluid. Their subcutaneous (0.63±0.06 g, p<0.01 vs HF) and visceral fat content (1.60±0.08 g, p<0.01 vs HF) were virtually identical to that seen in the 25 mg/kg I.P. every 8 day group. The fluid retention was not surprising given the substantial sodium load by the vehicle every 2 days along with the role of Na/K-ATPase signaling in the adaptive natriuresis with salt loading.

Blood Measurements of Adiponectin.

High molecular weight (HMW) form of adiponectin was determined in serum using an ELISA assay according to the manufacture's protocol.

Western Blot Analysis.

Visceral fat was pulverized under liquid nitrogen and placed in a homogenization buffer. Homogenates were centrifuged, the supernatant was isolated, and immunoblotting was performed. The supernatant was used for the determination of FAS, Adiponectin, PPARγ and MEST. β Actin was used to ensure adequate sample loading for all Western blots as described previously.

Measurement of c-Src and ERK1/2 Phosphorylation.

Visceral fat and whole cell lysates obtained from 3T3L1 adipocytes were prepared with Nonidet P-40 buffer and activation of c-Src and ERK1/2 was determined as described previously. After immunoblotting for phospho-c-Src and phospho-ERK1/2, the same membrane was stripped and immunoblotted for total c-Src and total ERK1/2. Activation of c-Src and ERK1/2 was expressed as the ratio of phospho-c-Src/total-Src and phospho-ERK1/2/total-ERK1/2 respectively, with both measurements normalized to 1.0 for the control samples.

Assessment of Protein Carbonylation.

Visceral fat and whole cell lysates were prepared with Nonidet P-40 buffer and western blotting for protein carbonylation assay was done. The signal density values of control samples were normalized to 1.0 with Ponceau S staining as loading control.

Glucose Tolerance Test.

Glucose clearance was determined using an intraperitoneal glucose tolerance test before termination of the experiment. Mice were made to fast for 8 h after which a glucose solution (2 g/kg body weight, injected as a 10% solution) was injected into the peritoneal cavity. Samples were taken from the tail vein at 0, 30, 60 and 120 min after glucose injection. Blood glucose was measured using the Accutrend Sensor glucometer.

Determination of Homeostasis Model Assessment of Insulin Resistance.

The homeostasis model assessment of insulin resistance (HOMA-IR) was calculated from mice blood using glucose and insulin concentrations obtained after 8 h of food withdrawal, using the following formula: HOMA-IR=[fasting insulin (ng/ml)×fasting glucose (mmol/L)]/22.5.

Lipid Peroxidation Measurement.

Visceral fat lipid peroxidation was measured as Thiobarbituric acid reactive substance (TBARS) using an assay kit according to the manufacturer's protocol. Visceral fat samples were homogenized in a buffer solution containing 50 mM Tris-HCl (pH 7.4) and 1.15% KCl, and then centrifuged. The supernatant was used for the assay. Data was normalized to total protein and presented as micromoles/mg protein.

Distribution of Rhodamine B Labeled pNaKtide.

For in vitro study, murine pre-adipocytes (3T3L1) were grown on glass coverslips and treated with or without rhodamine B labeled pNaKtide (2 µM). At indicated time points, the cells were fixed with cold absolute methanol and mounted with DAPI mounting medium (Vector Labs). The images were taken (emission readings for DAPI and rhodamine B are 415-475 nm and 580-650 nm, respectively) with a Leica SP5 TCS II equipped with coherent chameleon multiphoton vision II (IR) laser and analyzed by Leica LAS/AF software. For in vivo study, mice were injected (by i.p.) without (as control) or with rhodamine B labeled pNaKtide (25 mg/Kg body weight). Three hours after injection, the mice were sacrificed and the adipose tissues were imaged and analyzed as described above.

Statistical Analyses.

Statistical significance between experimental groups was determined by the Fisher method of analysis of multiple comparisons (p<0.05). For comparisons among treatment groups, the null hypothesis was tested by a two-factor ANOVA for multiple groups or unpaired t test for two groups. Data are presented as mean±SE.

Example 1—Effect of pNaKtide on Adipogenesis in Murine Pre-Adipocytes

Figure 1B:
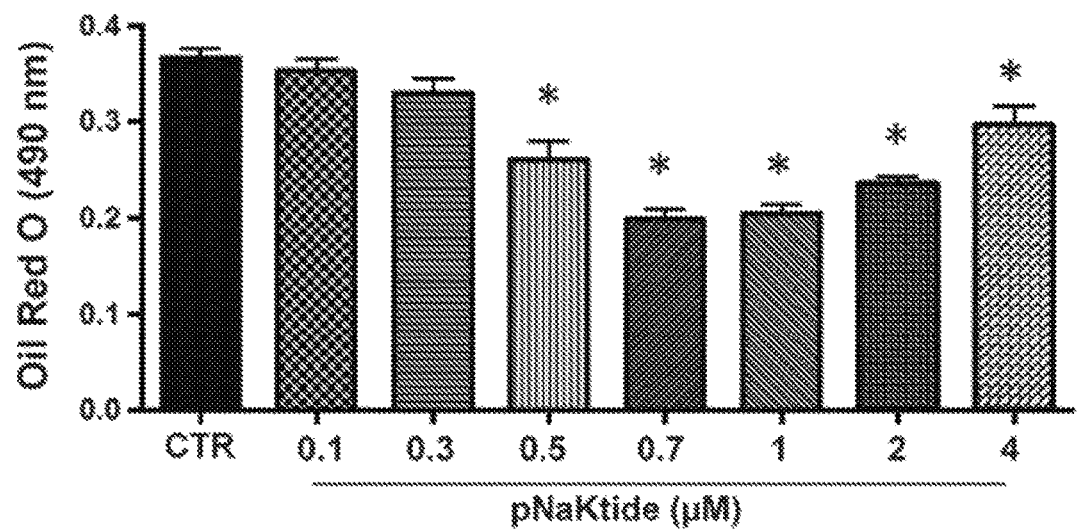
Figure 1C:
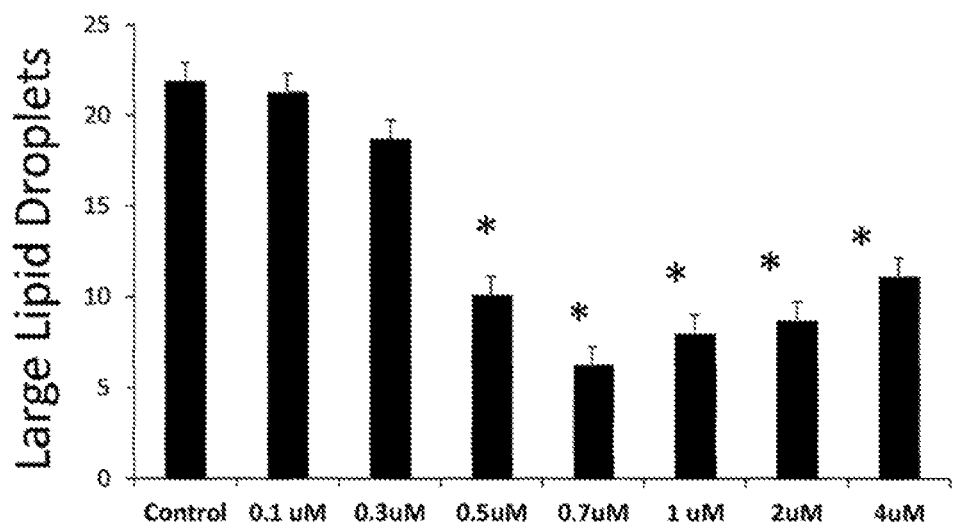
Figure 1D:
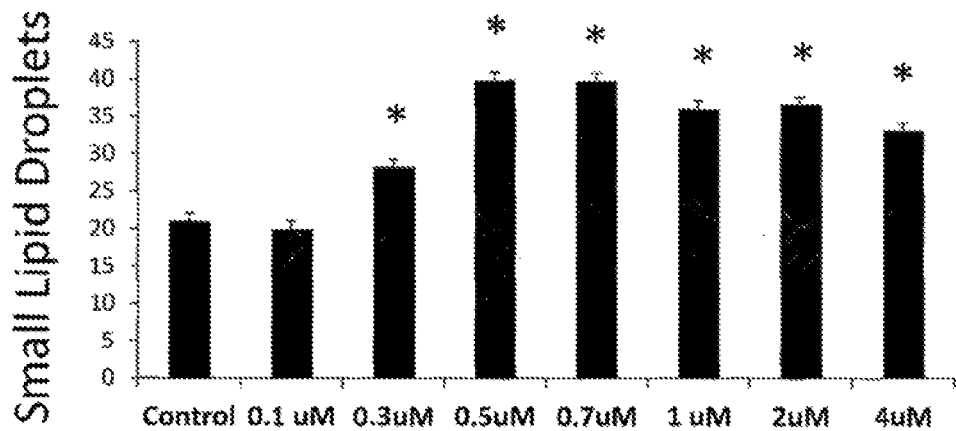
Figure 1E:
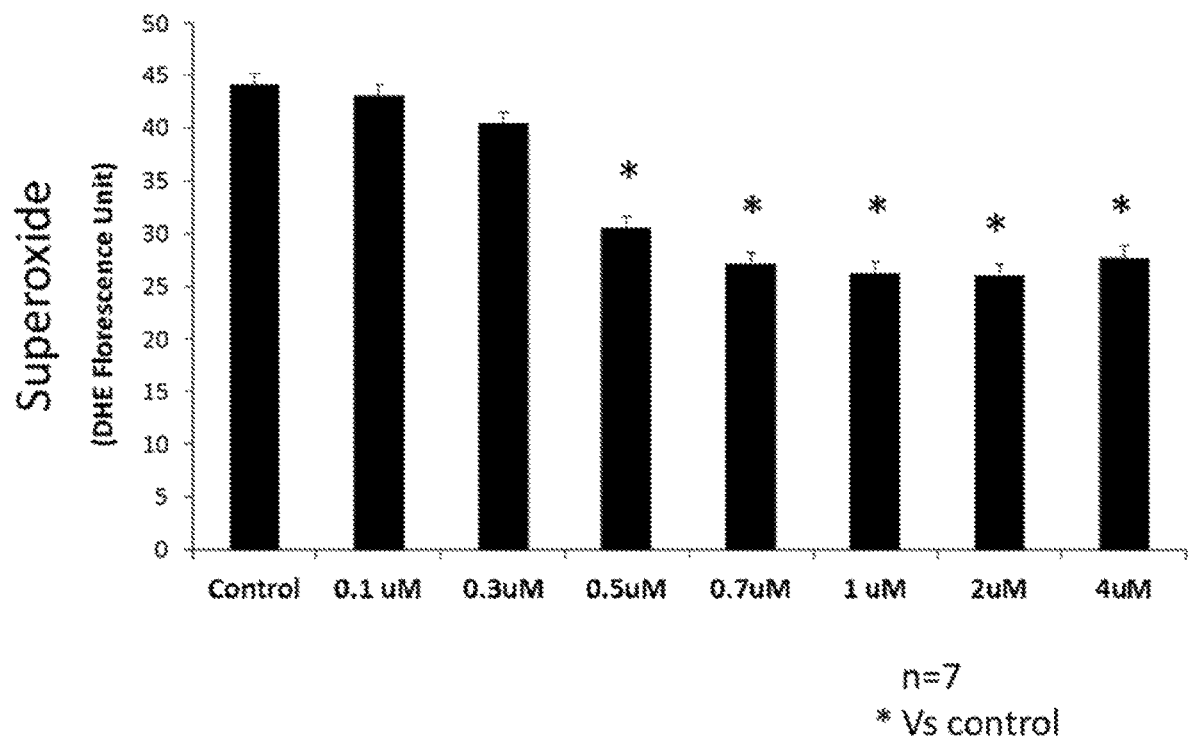

3T3L1 cells were exposed to adipogenic media and treated with increasing doses of pNaKtide. Results showed that pNaKtide reduced lipid accumulation (FIG. 1A) in 3T3L1 cells in a dose-dependent manner. As a control, these cells were exposed to rhodamine-labeled pNaKtide and it was found that pNaKtide readily passed cell membrane and resided in the intracellular membrane compartments (FIG. 1B). In addition to decreasing the net accumulation of lipid, pNaKtide also increased the amount of lipid in small droplets while decreasing the proportion in large droplets, also in a dose-dependent manner (FIGS. 1C and 1D, respectively). Oxidative stress is one of the consequences of Na/K-ATPase activation. Superoxide levels, a marker for oxidative stress, were reduced significantly by pNaKtide in 3T3L1 cells (FIG. 1E; p<0.05). No cytotoxic effects of pNaKtide were noted at studied doses (up to 4 µmol/l).

Figure 2A:
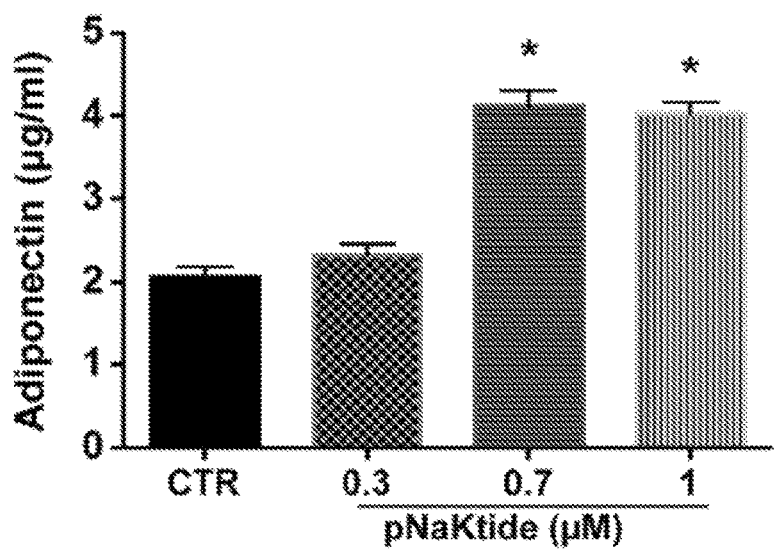
FIGS. 2A-2D include images and graphs showing that pNaKtide increased adiponectin levels and decreased adipogenic markers in 3T3L1 adipocytes, including.
Figure 2B:
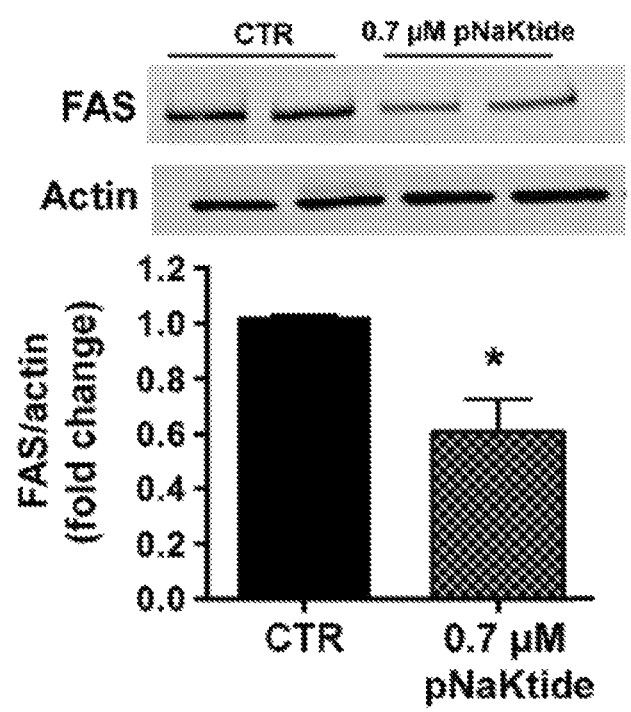
Figure 2C:
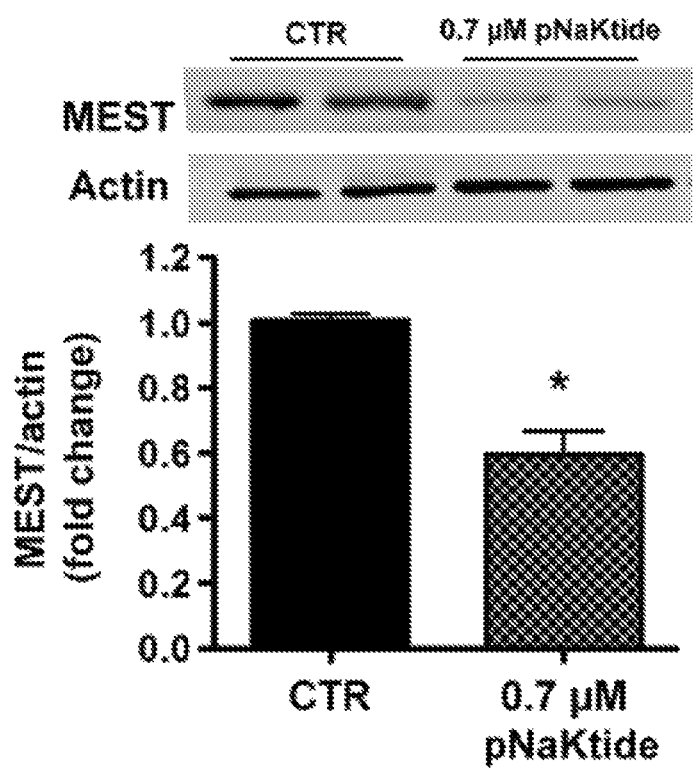
Figure 2D:
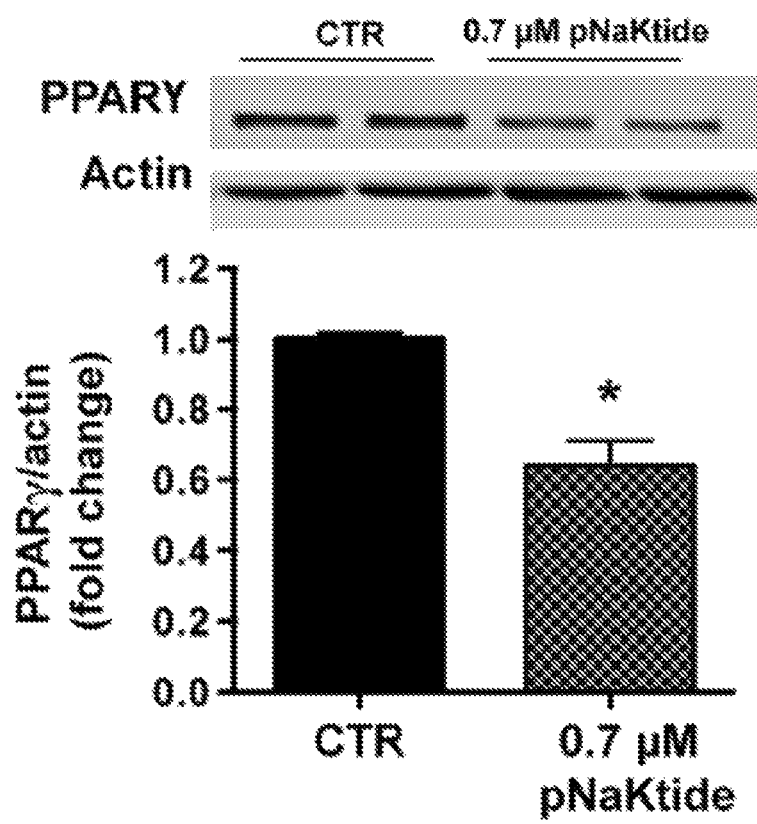

Example 2—Effect of pNaKtide on Adiponectin Levels and Adipogenic Markers in Murine Pre-Adipocytes Administration of pNaKtide increased adiponectin levels (FIG. 2A; p<0.05), a known marker of small insulin-sensitive and healthy adipocytes. Furthermore, results showed that pNaKtide treatment significantly reduced the expression of adipogenic markers, including FAS, MEST and PPARγ (FIGS. 2B-2D, respectively). Thus, pNaKtide prevented adipocyte dysfunction, an effect that could, and without wishing to be bound by any particular theory, be attributed to its role on cellular redox through the Na/K-ATPase signal cascade.

Fructose has been shown to induce oxidative stress and increase adipogenesis in adipocytes exposed to adipogenic media. In the present studies, the fructose—induced increase in adipogenesis was prevented by treatment with pNaKtide in 3T3L1 cells. Similarly, addition of glucose oxidase to the adipogenic media also increased lipid accumulation and adipogenic markers, FAS and MEST in 3T3L1 cells, and this was significantly attenuated by concurrent treatment with pNaKtide. Treatment with pNaKtide also decreased protein carbonylation and also blocked Na/K-ATPase-regulated Src and extracellular signal-regulated kinases (ERK) 1 and 2 activation in 3T3L1 cells exposed to glucose oxidase.

Figure 3:
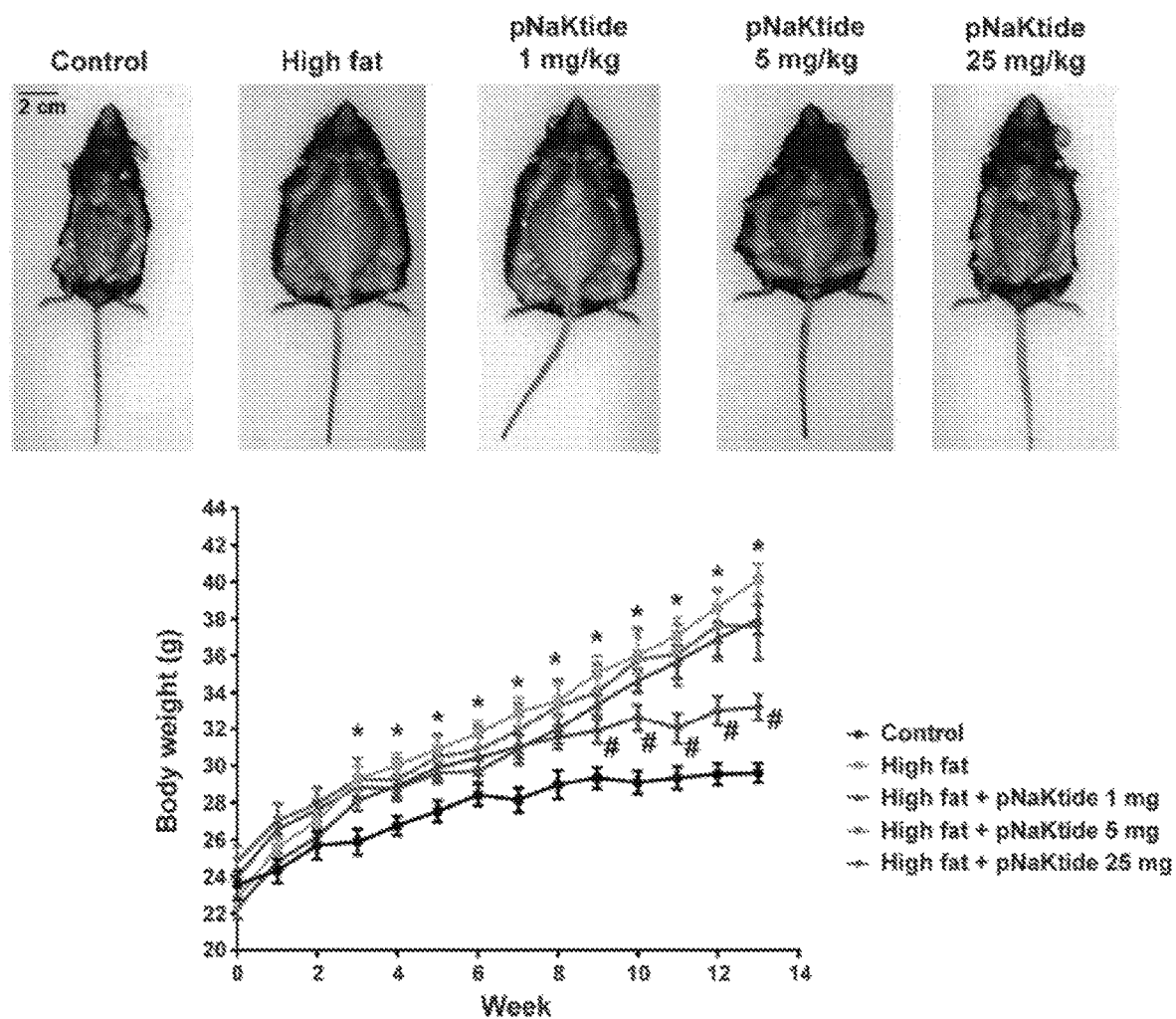
FIG. 3 includes images and a graph showing the effect of increasing doses of pNaKtide on body weight in mice fed a high-fat diet, where C57B16 mice injected with 1 mg/kg and 5-mg/kg body weights doses of pNaKtide, respectively, had no significant reduction in body weight in mice fed a high-fat diet, where 25-mg/kg body weight administration of pNaKtide every 8 days in mice fed a high-fat diet for 8 weeks significantly reduced body weight as compared to high-fat diet fed animals, and where there were no significant changes in food intake among the groups (results are means±SE, n=7-14/group, *p<0.05 vs. control, # vs. high fat (HF) diet).
Figure 4A:
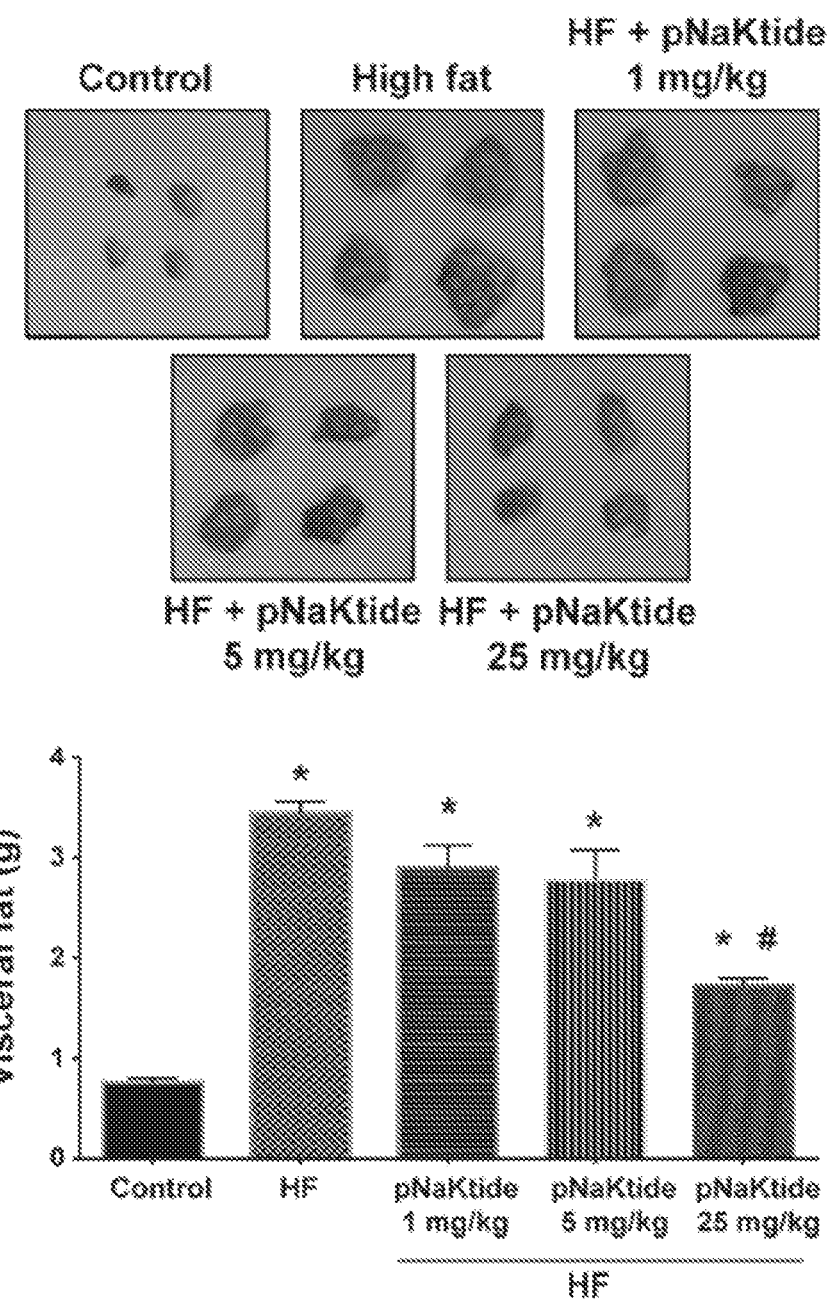
FIGS. 4A-4B include images and graphs showing the effect of increasing doses of pNaKtide on visceral and subcutaneous fat content in mice fed a high-fat diet, where C57B16 mice were injected with 1 mg/kg, 5 mg/kg, and 25 mg/kg body weights doses of pNaKtide every 8 days respectively in mice fed a high-fat diet for 8 weeks, and where 25 mg/kg body weight administration of pNaKtide in mice fed a high-fat diet significantly reduced visceral (FIG. 4A) and subcutaneous (FIG. 4B) fat content as compared to high-fat diet fed animals (results are means±SE, n=7-14/group, *p<0.05 vs. control, # vs. HF).
Figure 4B:
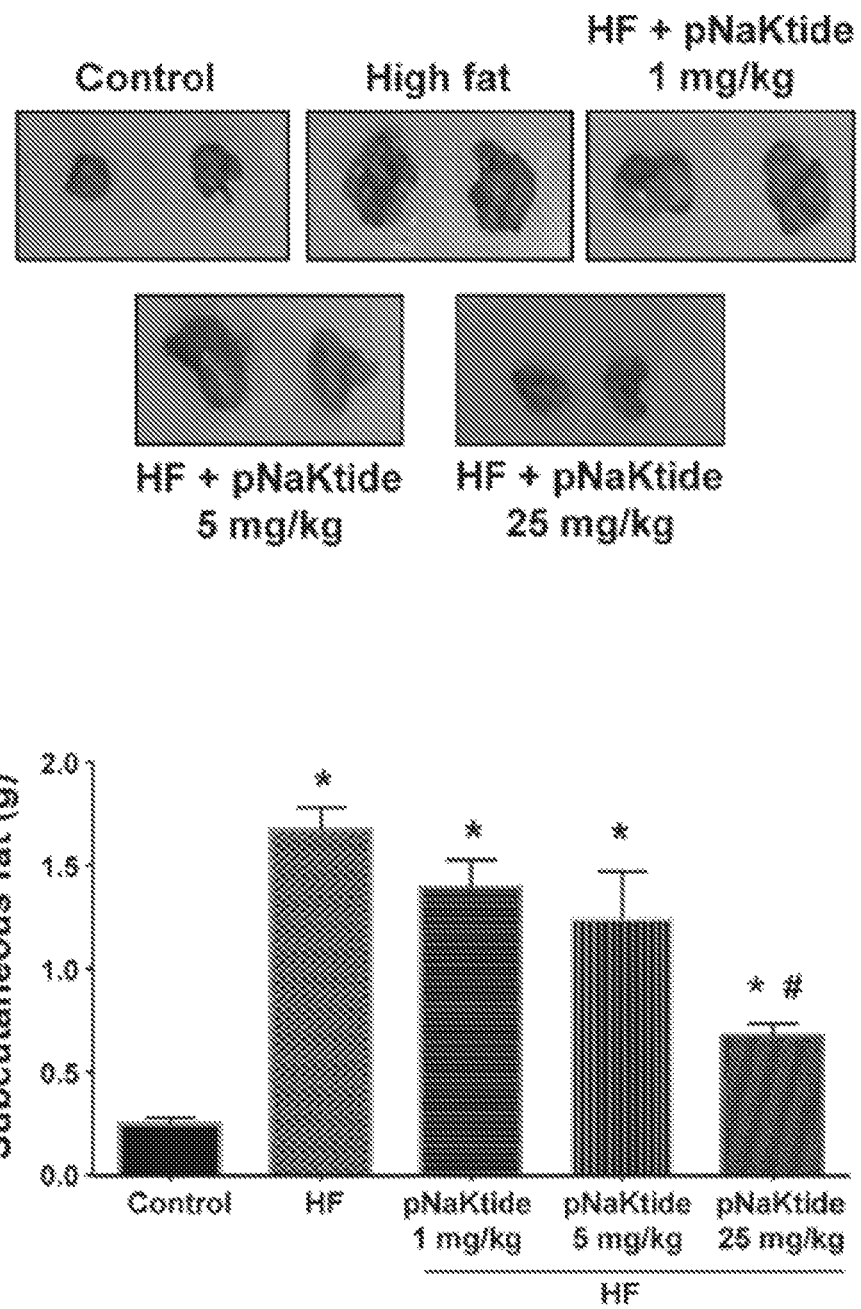

Example 3—Effect of pNaKtide on Body Weight and Visceral and Subcutaneous Fat Content in Mice Fed a High-Fat Diet For in vivo studies, C57B16 mice were exposed to a high-fat diet for 4 weeks and then given pNaKtide at different dosages through IP injection while the high-fat diet was continued for another 8 weeks. In parallel experiments, rhodamine-labeled peptide was demonstrated to accumulate in adipose tissue. The administration of pNaKtide at 25 mg/kg IP every 8 days dramatically reduced adiposity in these mice with lower doses having less effects (FIGS. 3 and 4A-4B). However, pNaKtide administered more frequently (25 mg/kg IP every 2 days) induced some fluid retention, and therefore subsequent studies were focused on the effects of pNaKtide on adipogenic markers and metabolic profile when given every 8 days.

Figure 5A:
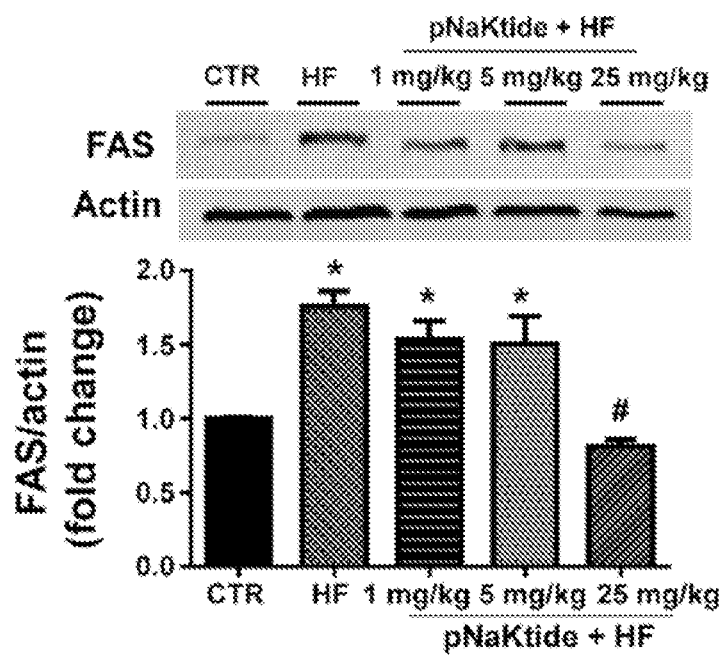
FIGS. 5A-5C include images and graphs showing the effect of increasing doses of pNaKtide on adipogenic markers and adiponectin expression in visceral adipose tissue in mice fed a high-fat diet, including: western blot and densitometry analysis of adipogenic markers in visceral adipose tissue (FIG. 5A) FAS and (FIG. 5B) MEST (results are means±SE, n=7/group, *p<0.05 vs. control, # vs. HF; data are shown as mean band density normalized to β-actin)
Figure 5B:
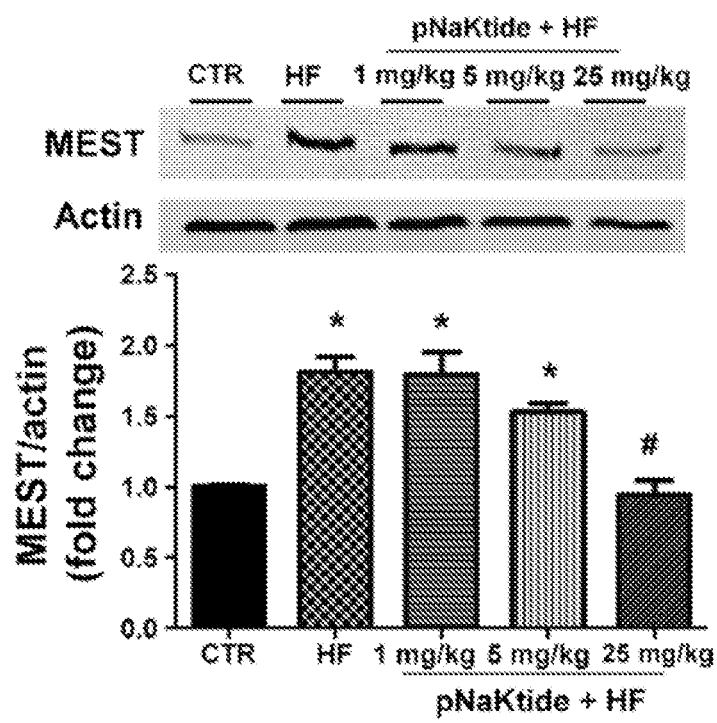
Figure 5C:
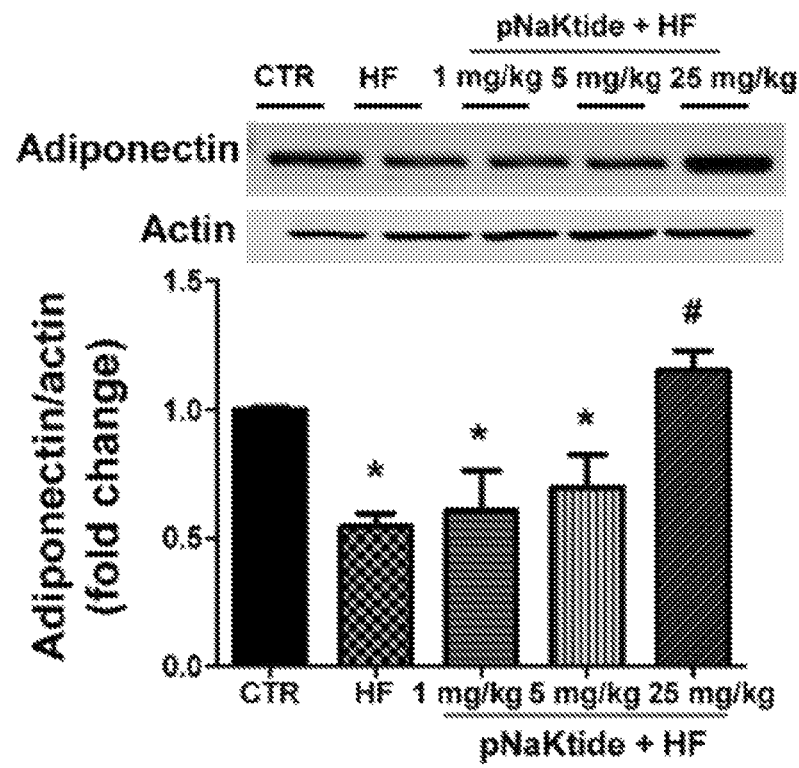

Example 4—Effect of pNaKtide on Adipogenic Markers and Adiponectin Expression in Mice Fed a High-Fat Diet Mice fed a high-fat diet exhibited an increase in FAS (FIG. 5A) and MEST (FIG. 5B) gene expression in visceral adipose tissue compared to the control group. Treatment with pNaKtide (25 mg/kg body weight every 8 days) significantly decreased FAS and MEST levels compared to mice fed a high-fat diet. Further, the results showed that pNaKtide treatment increased adiponectin levels in visceral adipose tissue compared to the mice fed a high-fat diet (FIG. 5C). These observations support the hypothesis that pNaKtide not only reduced adipose tissue mass, but also promoted development of healthier adipocytes, with adiponectin levels comparable to those seen with regular diet.

Example 5—Effect of pNaKtide on Metabolic Profile in Mice Fed a High-Fat Diet

Figure 6A:
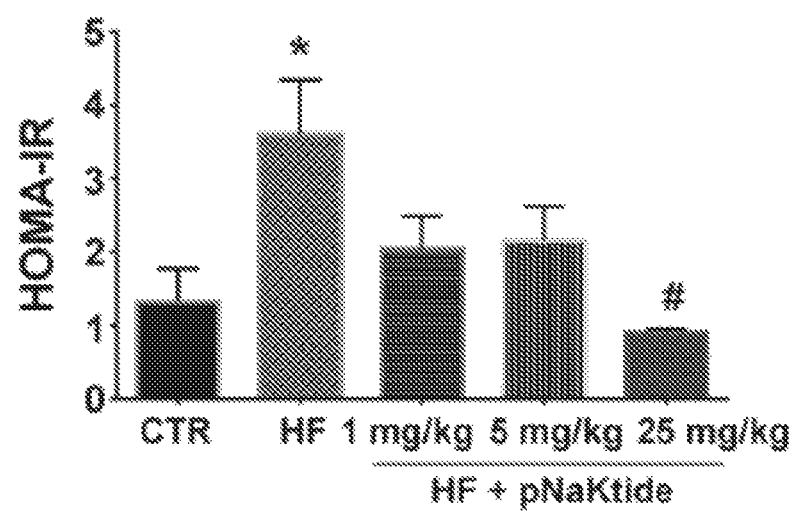
FIGS. 6A-6G include graphs and images showing the effect of increasing doses of pNaKtide on metabolic profile in mice fed a high-fat diet. These figures includes graphs showing.
Figure 6B:
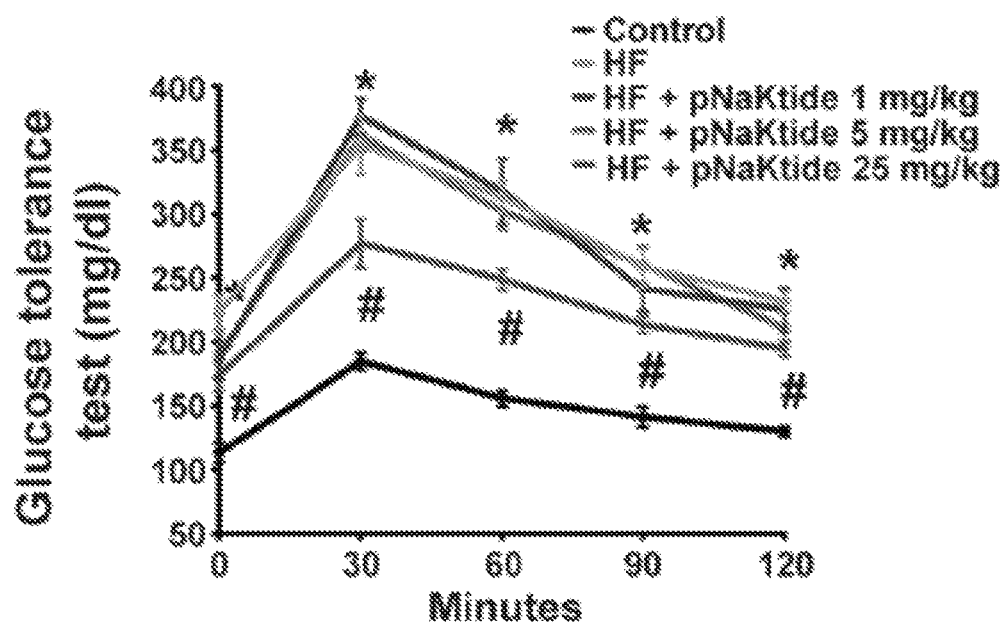
Figure 6C:
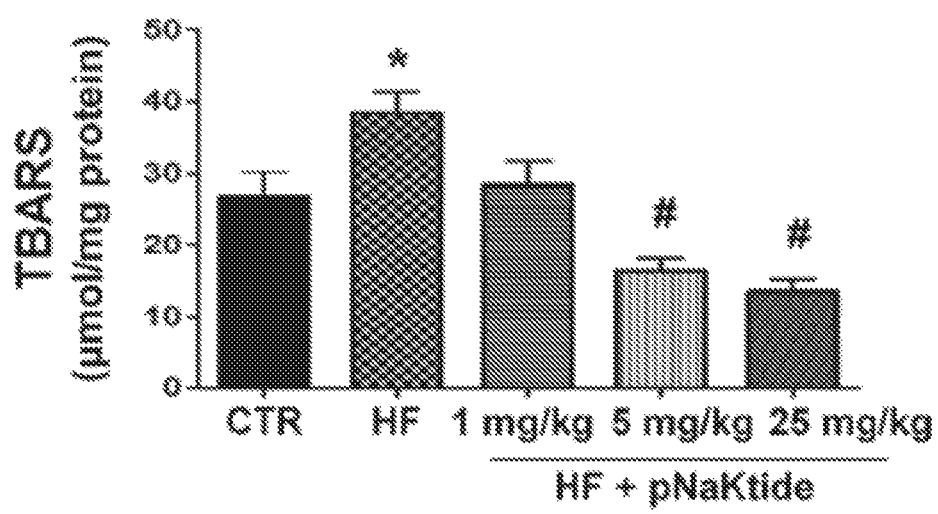
Figure 6D:
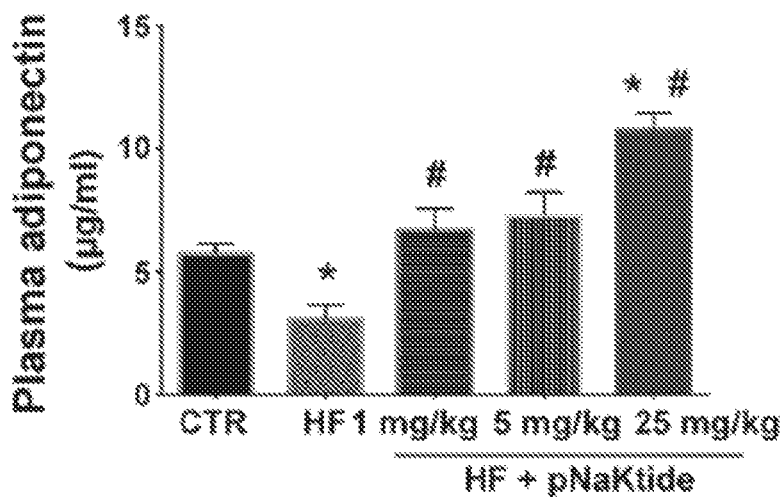
Figure 6E:
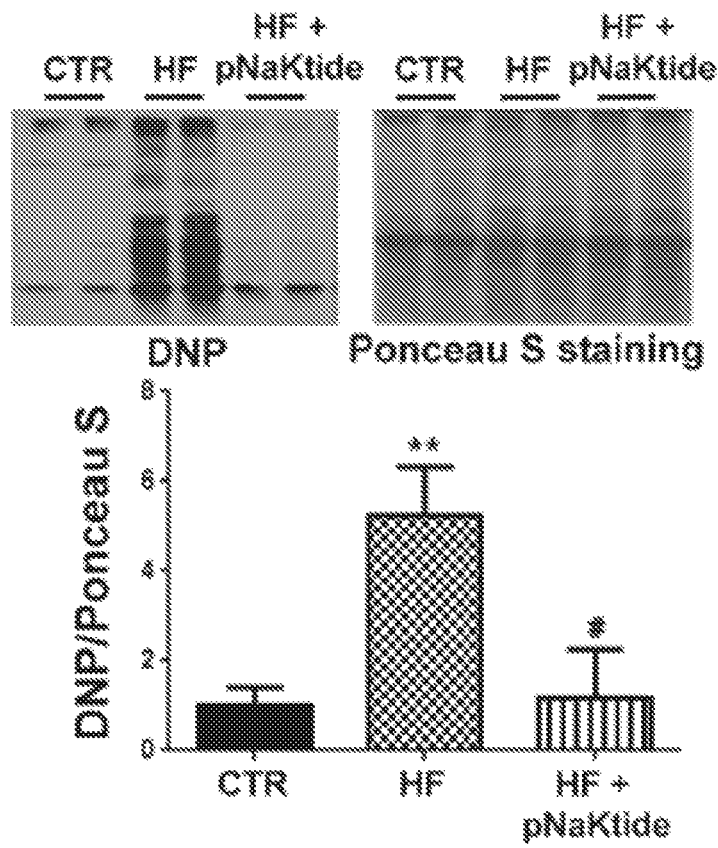
Figure 6F:
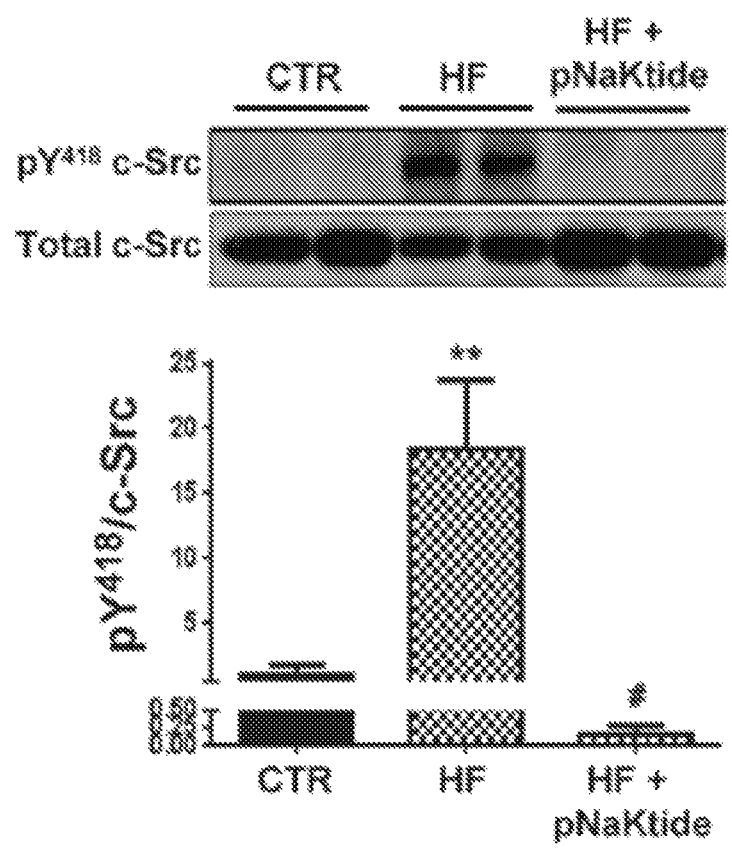
Figure 6G:
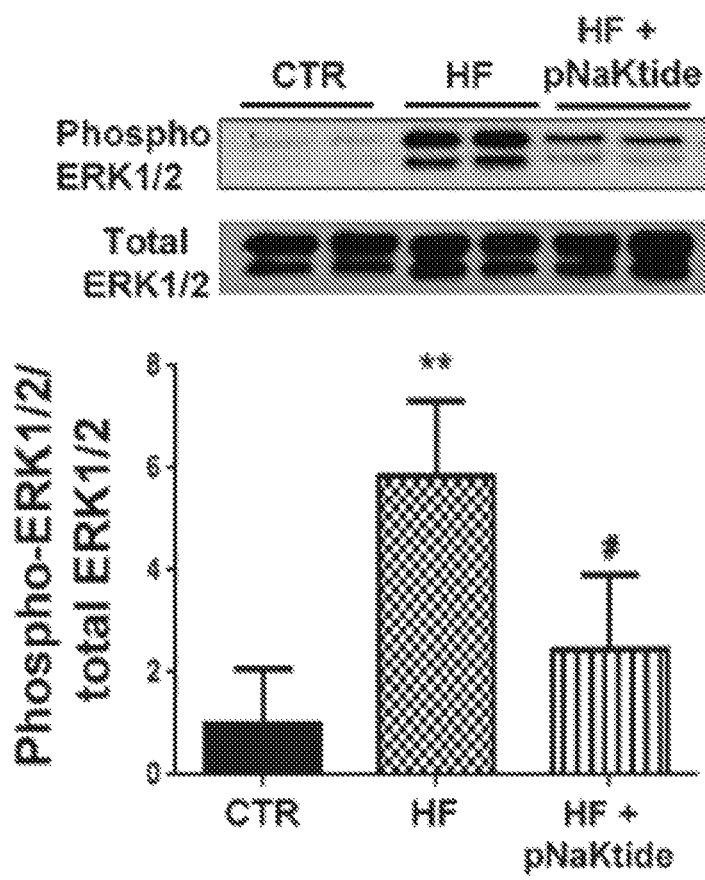

The insulin resistance phenotype in mice fed a high-fat diet was reversed by the administration of pNaKtide. This was characterized by significant improvements in the HOMA-IR score (FIG. 6A), improved glucose tolerance (FIG. 6B), attenuation of oxidative stress in visceral adipose tissue (FIG. 6C), and significantly elevated levels of circulating adiponectin in mice concurrently treated with the peptide (FIG. 6D). The administration of pNaKtide also significantly attenuated high-fat diet-induced protein carbonylation in visceral adipose tissue (FIG. 6E) and the activation of c-Src and ERK1/2 in mice fed a high-fat diet (FIGS. 6F and 6G).

Discussion of Examples 1-5

The foregoing studies characterized the therapeutic potential of pNaKtide for conditions associated with obesity and metabolic imbalance. Oxidative stress, a frequent accompaniment of chronic pathologies, has long been implicated in the pathogenesis of adiposity. A plethora of antioxidants have shown promise in reversing this effect in in vitro studies, with few in vivo successes. The foregoing studies demonstrate that pNaKtide effectively reduces adiposity and restores metabolic homeostasis by antagonizing Na/K-ATPase-mediated amplification of ROS signaling.

It was also observed that in murine preadipocytes, exposure to pNaKtide attenuated oxidative stress as well as the accumulation of lipid and the manifestations of an obesity phenotype in a dose—dependent manner in response to either adipogenic media or exogenous administration of oxidative stress mediators, fructose or glucose oxidase. That decrease in adipogenesis in murine preadipocytes treated with pNaKtide was associated with significantly decreased expression of adipogenic regulators including PPARγ and FAS along with increased production of adiponectin levels. Thus, the Na/K-ATPase inhibitor prevents dysfunctional adipogenesis, an effect that could be attributed to its effects on cellular redox. Moving to an in vivo model of obesity induced by a high-fat diet, it was again observed that intraperitoneal administration of pNaKtide attenuated the development of obesity and the development of metabolic syndrome. pNaKtide treatment resulted in significant reduction in weight gain complemented by attenuation of visceral and subcutaneous fat content in mice fed a high-fat diet. Dysfunctional adipocytes are associated with the development of insulin resistance and hyperglycemia, and they favor a proinflammatory state. Severe insulin resistance, systemic inflammation, and dysregulation of protective adipokines characterize metabolic syndrome. The above-described results showed that pNaKtide decreased oxidative stress and insulin resistance with an increase in adiponectin levels. It was further demonstrated that a decrease in obesity was associated with changes in adipogenic proteins. Mice fed a high-fat diet and treated with pNaKtide displayed decreased levels of MEST and FAS expression further demonstrating the pNaKtide-mediated abrogation of adiposity and metabolic imbalance.

These observations were of potential interest for several reasons. First, the studies clearly demonstrated the ability of the Na/K-ATPase signal cascade to amplify ROS involved in adipogenesis, a process not previously linked to cardiotonic steroids or the Na/K-ATPase signal cascade. However, perhaps of greater import, the concept that ROS amplification can occur through this pathway indicates the Na/K-ATPase may serve as a potential therapeutic target in a number of conditions characterized by oxidative stress, which ultimately becomes maladaptive. Perhaps because pNaKtide targets the amplification of oxidants rather than a primary signal cascade, it can provide new approaches for the treatment of obesity and metabolic syndrome.

Throughout this document, various references are mentioned. All such references are incorporated herein by reference, including the references set forth in the following list:

1. International Patent Application Publication No. WO 2008/054792, of Xie, entitled "Na/K-ATPase-Specific Peptide Inhibitors/Activators of Src and Src Family Kinases."
2. International Patent Application Publication No. WO 2010/071767, of Xie, entitled "Na/K-ATPase-Derived Src Inhibitors and Ouabain Antagonists and Uses Thereof."
3. Wang, et al. "Involvement of Na/K-ATPase in hydrogen peroxide-induced activation of the Src/ERK pathway in LLC-PK1 cells." Free Radical Biology and Medicine. 2014, 71: 415-426.
4. Yan, et al. "Involvement of Reactive Oxygen Species in a Feed-forward Mechanism of Na/K-ATPase-mediated Signaling Transduction." Journal of Biological Chemistry. 2013, 288: 34249-34258.
5. A. R. Johnson, L. Makowski, Nutrition and metabolic correlates of obesity and inflammation: clinical considerations. The Journal of nutrition 145, 1131S-1136S (2015); published online Epub May (10.3945/jn.114.200758).
6. A. Burgess, M. Li, L. Vanella, D. H. Kim, R. Rezzani, L. Rodella, K. Sodhi, M. Canestraro, P. Martasek, S. J. Peterson, A. Kappas, N. G. Abraham, Adipocyte heme oxygenase-1 induction attenuates metabolic syndrome in both male and female obese mice. Hypertension 56, 1124-1130 (2010); published online Epub December (10.1161/HYPERTENSIONAHA.110.151423).
7. M. Li, D. H. Kim, P. L. Tsenovoy, S. J. Peterson, R. Rezzani, L. F. Rodella, W. S. Aronow, S. Ikehara, N. G. Abraham, Treatment of obese diabetic mice with a heme oxygenase inducer reduces visceral and subcutaneous adiposity, increases adiponectin levels, and improves insulin sensitivity and glucose tolerance. Diabetes 57, 1526-1535 (2008); published online Epub June (10.2337/db07-1764).
8. M. Lafontan, Adipose tissue and adipocyte dysregulation. Diabetes & metabolism 40, 16-28 (2014); published online Epub February (10.1016/j.diabet.2013.08.002).
9. A. B. Crujeiras, A. Diaz-Lagares, M. C. Carreira, M. Amil, F. F. Casanueva, Oxidative stress associated to dysfunctional adipose tissue: a potential link between obesity, type 2 diabetes mellitus and breast cancer. Free radical research 47, 243-256 (2013); published online Epub April (10.3109/10715762.2013.772604).
10. A. Galinier, A. Carriere, Y. Fernandez, C. Carpene, M. Andre, S. Caspar-Bauguil, J. P. Thouvenot, B. Periquet, L. Penicaud, L. Casteilla, Adipose tissue proadipogenic redox changes in obesity. The Journal of biological chemistry 281, 12682-12687 (2006); published online Epub May 5 (10.1074/jbc.M506949200).
11. S. Furukawa, T. Fujita, M. Shimabukuro, M. Iwaki, Y. Yamada, Y. Nakajima, O. Nakayama, M. Makishima, M. Matsuda, I. Shimomura, Increased oxidative stress in obesity and its impact on metabolic syndrome. The Journal of clinical investigation 114, 1752-1761 (2004); published online Epub December (10.1172/JCI21625).
12. C. K. Roberts, R. J. Barnard, R. K. Sindhu, M. Jurczak, A. Ehdaie, N. D. Vaziri, Oxidative stress and dysregulation of NAD(P)H oxidase and antioxidant enzymes in diet-induced metabolic syndrome. Metabolism: clinical and experimental 55, 928-934 (2006); published online Epub July (10.1016/j.metabol.2006.02.022).
13. L. Vanella, K. Sodhi, D. H. Kim, N. Puri, M. Maheshwari, T. D. Hinds, L. Bellner, D. Goldstein, S. J. Peterson, J. I. Shapiro, N. G. Abraham, Increased heme-oxygenase 1 expression in mesenchymal stem cell-derived adipocytes decreases differentiation and lipid accumulation via upregulation of the canonical Wnt signaling cascade. Stem cell research & therapy 4, 28 (2013)10.1186/scrt176).
14. A. Nicolai, M. Li, D. H. Kim, S. J. Peterson, L. Vanella, V. Positano, A. Gastaldelli, R. Rezzani, L. F. Rodella, G. Drummond, C. Kusmic, A. L'Abbate, A. Kappas, N. G. Abraham, Heme oxygenase-1 induction remodels adipose tissue and improves insulin sensitivity in obesity-induced diabetic rats. Hypertension 53, 508-515 (2009); published online Epub March (10.1161/HYPERTENSIONAHA.108.124701).
15. S. J. Peterson, G. Drummond, D. H. Kim, M. Li, A. L. Kruger, S. Ikehara, N. G. Abraham, L-4F treatment reduces adiposity, increases adiponectin levels, and improves insulin sensitivity in obese mice. Journal of lipid research 49, 1658-1669 (2008); published online Epub August (10.1194/jlr.M800046-JLR200).
16. J. Cao, S. J. Peterson, K. Sodhi, L. Vanella, I. Barbagallo, L. F. Rodella, M. L. Schwartzman, N. G. Abraham, A. Kappas, Heme oxygenase gene targeting to adipocytes attenuates adiposity and vascular dysfunction in mice fed a high-fat diet. Hypertension 60, 467-475 (2012); published online Epub August (10.1161/HYPERTENSIONAHA.112.193805).
17. N. G. Abraham, E. J. Brunner, J. W. Eriksson, R. P. Robertson, Metabolic syndrome: psychosocial, neuroendocrine, and classical risk factors in type 2 diabetes. Annals of the New York Academy of Sciences 1113, 256-275 (2007); published online Epub October (10.1196/annals.1391.015).
18. K. Sodhi, N. Puri, K. Inoue, J. R. Falck, M. L. Schwartzman, N. G. Abraham, EET agonist prevents adiposity and vascular dysfunction in rats fed a high fat diet via a decrease in Bach 1 and an increase in HO-1 levels. Prostaglandins & other lipid mediators 98, 133-142 (2012); published online Epub August (10.1016/j.prostaglandins.2011.12.004).
19. A. Iyer, D. P. Fairlie, J. B. Prins, B. D. Hammock, L. Brown, Inflammatory lipid mediators in adipocyte function and obesity. Nature reviews. Endocrinology 6, 71-82 (2010); published online Epub February (10.1038/nrendo.2009.264).
20. N. Puri, K. Sodhi, M. Haarstad, D. H. Kim, S. Bohinc, E. Foglio, G. Favero, N. G. Abraham, Heme induced oxidative stress attenuates sirtuin1 and enhances adipogenesis in mesenchymal stem cells and mouse pre-adipocytes. Journal of cellular biochemistry 113, 1926-1935 (2012); published online Epub June (10.1002/jcb.24061).
21. M. Takahashi, Y. Kamei, O. Ezaki, Mest/Peg1 imprinted gene enlarges adipocytes and is a marker of adipocyte size. American journal of physiology. Endocrinology and metabolism 288, E117-124 (2005); published online Epub January (10.1152/ajpendo.00244.2004).
22. D. H. Kim, A. P. Burgess, M. Li, P. L. Tsenovoy, F. Addabbo, J. A. McClung, N. Puri, N. G. Abraham, Heme oxygenase-mediated increases in adiponectin decrease fat content and inflammatory cytokines tumor necrosis factor-alpha and interleukin-6 in Zucker rats and reduce adipogenesis in human mesenchymal stem cells. The Journal of pharmacology and experimental therapeutics 325, 833-840 (2008); published online Epub June (10.1124/jpet.107.135285).
23. I. B. Bauche, S. A. El Mkadem, A. M. Pottier, M. Senou, M. C. Many, R. Rersohazy, L. Penicaud, N. Maeda, T. Funahashi, S. M. Brichard, Overexpression of adiponectin targeted to adipose tissue in transgenic mice: impaired adipocyte differentiation. Endocrinology 148, 1539-1549 (2007); published online Epub April (10.1210/en.2006-0838).
24. A. H. Berg, T. P. Combs, P. E. Scherer, ACRP30/adiponectin: an adipokine regulating glucose and lipid metabolism. Trends in endocrinology and metabolism: TEM 13, 84-89 (2002); published online Epub March (
25. A. Y. Bagrov, J. I. Shapiro, 0. V. Fedorova, Endogenous cardiotonic steroids: physiology, pharmacology, and novel therapeutic targets. Pharmacological reviews 61, 9-38 (2009); published online Epub March (10.1124/pr.108.000711).
26. K. J. Sweadner, Isozymes of the Na+/K+-ATPase. Biochimica et biophysica acta 988, 185-220 (1989); published online Epub May 9 (
27. M. Liang, J. Tian, L. Liu, S. Pierre, J. Liu, J. Shapiro, Z. J. Xie, Identification of a pool of non-pumping Na/K-ATPase. The Journal of biological chemistry 282, 10585-10593 (2007); published online Epub April 6 (10.1074/jbc.M609181200).
28. Y. Yan, S. Haller, A. Shapiro, N. Malhotra, J. Tian, Z. Xie, D. Malhotra, J. I. Shapiro, J. Liu, Ouabain-stimulated trafficking regulation of the Na/K-ATPase and NHE3 in renal proximal tubule cells. Molecular and cellular biochemistry 367, 175-183 (2012); published online Epub August (10.1007/s11010-012-1331-x).
29. J. Liu, Y. Yan, L. Liu, Z. Xie, D. Malhotra, B. Joe, J. I. Shapiro, Impairment of Na/K-ATPase signaling in renal proximal tubule contributes to Dahl salt-sensitive hypertension. The Journal of biological chemistry 286, 22806-22813 (2011); published online Epub July 1 (10.1074/jbc.M111.246249).
30. J. Liu, J. Tian, M. Haas, J. I. Shapiro, A. Askari, Z. Xie, Ouabain interaction with cardiac Na+/K+-ATPase initiates signal cascades independent of changes in intracellular Na+ and Ca2+ concentrations. The Journal of biological chemistry 275, 27838-27844 (2000); published online Epub September 8 (10.1074/jbc.M002950200).
31. Z. Xie, P. Kometiani, J. Liu, J. Li, J. I. Shapiro, A. Askari, Intracellular reactive oxygen species mediate the linkage of Na+/K+-ATPase to hypertrophy and its marker genes in cardiac myocytes. The Journal of biological chemistry 274, 19323-19328 (1999); published online Epub July 2 (
32. Y. Yan, A. P. Shapiro, S. Haller, V. Katragadda, L. Liu, J. Tian, V. Basrur, D. Malhotra, Z. J. Xie, N. G. Abraham, J. I. Shapiro, J. Liu, Involvement of reactive oxygen species in a feed-forward mechanism of Na/K-ATPase-mediated signaling transduction. The Journal of biological chemistry 288, 34249-34258 (2013); published online Epub November 22 (10.1074/jbc.M113.461020).
33. Y. Wang, Q. Ye, C. Liu, J. X. Xie, Y. Yan, F. Lai, Q. Duan, X. Li, J. Tian, Z. Xie, Involvement of Na/K-ATPase in hydrogen peroxide-induced activation of the Src/ERK pathway in LLC-PK1 cells. Free radical biology & medicine 71, 415-426 (2014); published online Epub June (10.1016/j.freeradbiomed.2014.03.036).
34. Z. Li, T. Cai, J. Tian, J. X. Xie, X. Zhao, L. Liu, J. I. Shapiro, Z. Xie, NaKtide, a Na/K-ATPase-derived peptide Src inhibitor, antagonizes ouabain-activated signal transduction in cultured cells. The Journal of biological chemistry 284, 21066-21076 (2009); published online Epub July 31 (10.1074/jbc.M109.013821).
35. J. Liu, D. J. Kennedy, Y. Yan, J. I. Shapiro, Reactive Oxygen Species Modulation of Na/K-ATPase Regulates 36. F. Lai, N. Madan, Q. Ye, Q. Duan, Z. Li, S. Wang, S. Si, Z. Xie, Identification of a mutant alpha1 Na/K-ATPase that pumps but is defective in signal transduction. The Journal of biological chemistry 288, 13295-13304 (2013); published online Epub May 10 (10.1074/jbc.M113.467381).
37. Z. Li, Z. Zhang, J. X. Xie, X. Li, J. Tian, T. Cai, H. Cui, H. Ding, J. I. Shapiro, Z. Xie, Na/K-ATPase mimetic pNaKtide peptide inhibits the growth of human cancer cells. The Journal of biological chemistry 286, 32394-32403 (2011); published online Epub September 16 (10.1074/jbc.M110.207597).
38. K. Sodhi, N. Puri, D. H. Kim, T. D. Hinds, L. A. Stechschulte, G. Favero, L. Rodella, J. I. Shapiro, D. Jude, N. G. Abraham, PPARdelta binding to heme oxygenase 1 promoter prevents angiotensin II-induced adipocyte dysfunction in Goldblatt hypertensive rats. International journal of obesity 38, 456-465 (2014); published online Epub March (10.1038/ijo.2013.116).
39. J. J. Diez, P. Iglesias, The role of the novel adipocyte-derived hormone adiponectin in human disease. European journal of endocrinology/European Federation of Endocrine Societies 148, 293-300 (2003); published online Epub March (
40. Z. Khitan, M. Harsh, K. Sodhi, J. I. Shapiro, N. G. Abraham, HO-1 Upregulation Attenuates Adipocyte Dysfunction, Obesity, and Isoprostane Levels in Mice Fed High Fructose Diets. Journal of nutrition and metabolism 2014, 980547 (2014)10.1155/2014/980547).
41. G. Murdolo, M. Piroddi, F. Luchetti, C. Tortoioli, B. Canonico, C. Zerbinati, F. Galli, L. Iuliano, Oxidative stress and lipid peroxidation by-products at the crossroad between adipose organ dysregulation and obesity-linked insulin resistance. Biochimie 95, 585-594 (2013); published online Epub March (10.1016/j.biochi.2012.12.014).
42. A. P. Burgess, L. Vanella, L. Bellner, K. Gotlinger, J. R. Falck, N. G. Abraham, M. L. Schwartzman, A. Kappas, Heme oxygenase (HO-1) rescue of adipocyte dysfunction in HO-2 deficient mice via recruitment of epoxyeicosatrienoic acids (EETs) and adiponectin. Cellular physiology and biochemistry: international journal of experimental cellular physiology, biochemistry, and pharmacology 29, 99-110 (2012)10.1159/000337591).
43. J. Cheng, C. C. Wu, K. H. Gotlinger, F. Zhang, J. R. Falck, D. Narsimhaswamy, M. L. Schwartzman, 20-hydroxy-5,8,11,14-eicosatetraenoic acid mediates endothelial dysfunction via IkappaB kinase-dependent endothelial nitric-oxide synthase uncoupling. The Journal of pharmacology and experimental therapeutics 332, 57-65 (2010); published online Epub January (10.1124/jpet.109.159863).
44. K. Sodhi, K. Inoue, K. H. Gotlinger, M. Canestraro, L. Vanella, D. H. Kim, V. L. Manthati, S. R. Koduru, J. R. Falck, M. L. Schwartzman, N. G. Abraham, Epoxyeicosatrienoic acid agonist rescues the metabolic syndrome phenotype of HO-2-null mice. The Journal of pharmacology and experimental therapeutics 331, 906-916 (2009); published online Epub December (10.1124/jpet.109.157545)
45. U.S. Pat. No. 8,283,441.
46. U.S. Pat. No. 8,691,947.
47. U.S. patent application Ser. No. 13/166,252.
48. U.S. patent application Ser. No. 14/045,269.
49. U.S. patent application Ser. No. 14/399,625.

What is claimed is:

1. A method for treating obesity, comprising administering a polypeptide antagonist of a Na/K ATPase/Src receptor complex to a subject in need thereof, wherein the polypeptide anatagonist comprises the sequence of SEQ ID NO: 1, or a functional fragment thereof.

2. The method of claim 1, wherein the polypeptide antagonist further includes a cell penetrating polypeptide encoded by an amino acid sequence selected from the group consisting of SEQ ID NOS: 2-3.

3. The method of claim 1, wherein the administering step includes oral administration, transdermal administration, administration by inhalation, nasal administration, topical administration, intraaural administration, rectal administration, intravenous administration, intramuscular administration, subcutaneous administration, intravitreous administration, or combinations thereof.

4. The method of claim 1, wherein administering the polypeptide antagonist decreases lipid accumulation in a cell of the subject.

5. The method of claim 4, wherein administering the polypeptide antagonist comprises administering the polypeptide antagonist in an amount sufficient to decrease an amount of adipogenesis, decrease an amount of adipocyte differentiation, and/or increase an amount of small adipocytes in the subject.

6. The method of claim 1, wherein administering the polypeptide antagonist comprises administering the polypeptide antagonist in an amount sufficient to decrease an amount of inflammatory cytokines in the subject.

7. The method of claim 6, wherein the inflammatory cytokine is TNFα.

8. The method of claim 1, wherein administering the polypeptide comprises administering the polypeptide antagonist in an amount sufficient to increase an amount of adiponectin in the subject.

9. The method of claim 1, wherein administering the polypeptide comprises administering the polypeptide antagonist in an amount sufficient to reduce an expression level of an adipogenic marker in the subject.

10. The method of claim 9, wherein the adipogenic marker is selected from FAS, MEST, and PPARγ.

11. The method of claim 1, wherein administering the polypeptide comprises administering the polypeptide antagonist in an amount sufficient to reduce an amount of adiposity in the subject.

12. The method of claim 11, wherein administering the polypeptide comprises administering the polypeptide antagonist in an amount sufficient to reduce an amount of visceral fat and/or an amount of subcutaneous fat in the subject.

13. A method for reducing adiposity, comprising administering a polypeptide antagonist of a Na/K ATPase/Src receptor complex to a subject in need thereof wherein the polypeptide antagonist comprises the sequence of SEQ ID NO: 1, or a functional fragment thereof.

14. A method for reducing adipogenesis, comprising contacting a cell with a polypeptide antagonist of a Na/K ATPase/Src receptor complex wherein the polypeptide antagonist comprises the sequence of SEQ ID NO: 1, or a functional fragment thereof.

15. The method of claim 14, wherein the cell is a preadipocyte.

* * * * *

SEQUENCE LISTING

```
<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Ser Ala Thr Trp Leu Ala Leu Ser Arg Ile Ala Gly Leu Cys Asn Arg
1               5                   10                  15

Ala Val Phe Gln
            20

<210> SEQ ID NO 2
<211> LENGTH: 13
<212> TYPE: PRT
<213> ORGANISM: Human immunodeficiency virus

<400> SEQUENCE: 2

Gly Arg Lys Lys Arg Arg Gln Arg Arg Arg Pro Pro Gln
1               5                   10

<210> SEQ ID NO 3
<211> LENGTH: 16
<212> TYPE: PRT
<213> ORGANISM: Drosophila melanogaster

<400> SEQUENCE: 3

Arg Gln Ile Lys Ile Trp Phe Gln Asn Arg Arg Met Lys Trp Lys Lys
```

```
1               5               10              15

<210> SEQ ID NO 4
<211> LENGTH: 8
<212> TYPE: PRT
<213> ORGANISM: Homo sapiens

<400> SEQUENCE: 4

Lys Lys Gly Lys Lys Gly Lys Lys
1               5

<210> SEQ ID NO 5
<211> LENGTH: 33
<212> TYPE: PRT
<213> ORGANISM: Artificial Sequence
<220> FEATURE:
<223> OTHER INFORMATION: TAT NaKtide Fusion Polypeptide

<400> SEQUENCE: 5

Gly Arg Lys Lys Arg Arg Gln Arg Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln
```